United States Patent
De Vries et al.

(10) Patent No.: US 12,215,309 B2
(45) Date of Patent: Feb. 4, 2025

(54) IDENTIFICATION OF RARE PRODUCTS OF CROSSING ORGANISMS

(71) Applicant: Heineken Supply Chain B.V., Amsterdam (NL)

(72) Inventors: Arthur Roelof Gorter De Vries, Delft (NL); Charlotte Catharina Koster, Delft (NL); Jean-Marc Georges Daran, Delft (NL); Jan-Maarten Geertman, Amsterdam (NL); Niels Gerard Adriaan Kuijpers, Amsterdam (NL)

(73) Assignee: Heineken Supply Chain B.V., Amsterdam (NL)

( * ) Notice: Subject to any disclaimer, the term of this patent is extended or adjusted under 35 U.S.C. 154(b) by 1082 days.

(21) Appl. No.: 17/054,271

(22) PCT Filed: May 10, 2019

(86) PCT No.: PCT/NL2019/050279
§ 371 (c)(1),
(2) Date: Nov. 10, 2020

(87) PCT Pub. No.: WO2019/216769
PCT Pub. Date: Nov. 14, 2019

(65) Prior Publication Data
US 2021/0246415 A1 Aug. 12, 2021

(30) Foreign Application Priority Data
May 11, 2018 (NL) ..................................... 2020912

(51) Int. Cl.
| | |
|---|---|
| C12N 1/16 | (2006.01) |
| C12Q 1/6895 | (2018.01) |
| C12R 1/865 | (2006.01) |
| G01N 1/30 | (2006.01) |

(52) U.S. Cl.
CPC .............. *C12N 1/16* (2013.01); *C12Q 1/6895* (2013.01); *G01N 1/30* (2013.01); *C12R 2001/865* (2021.05)

(58) Field of Classification Search
None
See application file for complete search history.

(56) References Cited

U.S. PATENT DOCUMENTS

| | | |
|---|---|---|
| 4,812,405 A | 3/1989 | Lair et al. |
| 2008/0098496 A1 | 4/2008 | Van Dun et al. |
| 2018/0127784 A1 | 5/2018 | Alexander et al. |

FOREIGN PATENT DOCUMENTS

| | | |
|---|---|---|
| AU | 2004262040 A1 | 2/2005 |
| CN | 103458696 A | 12/2013 |
| CN | 103740821 A | 4/2014 |
| EA | 010892 B1 | 12/2008 |
| JP | H0372869 A | 3/1991 |
| JP | 10965874 A | 3/1997 |
| JP | H1066583 A | 3/1998 |
| WO | 9831824 A1 | 7/1998 |
| WO | 2009146617 A1 | 12/2009 |
| WO | 2013158539 A1 | 10/2013 |

OTHER PUBLICATIONS

Arthur R. Gorter De Vries et al, "Phenotype-Independent Isolation of Interspecies *Saccharomyces* Hybrids by Dual- Dye Fluorescent Staining and Fluorescence-Activated Cell Sorting", Frontiers in Microbiology, (Apr. 26, 2019), vol. 10, No. 871, doi:10.3389/fmicb.2019.00871, pp. 1-12.
Drew Thacker et al., "Exploiting Spore-Autonomous Fluorescent Protein Expression to Quantify Meiotic Chromosome Behaviors in *Saccharomyces cerevisiae*", Genetics, US, (Aug. 11, 2011), vol. 189, No. 2, doi: 10.1534/genetics.111.131326, ISSN 0016-6731, pp. 423-439.
David E. Block et al., "Rapid identification and isolation of zygotes and the kinetics of mating in *Saccharomyces cerevisiae*", Biotechnology Techniques., (Jan. 1, 1991), vol. 5, No. 2, doi:10.1007/BF00159978, ISSN 0951-208X, pp. 95-100.
P. J. L. Bell et al., "A Flow Cytometric Method for Rapid Selection of Novel Industrial Yeast Hybrids", Applied and Environmental Microbiology, United States, (May 1, 1998), pp. 1669-1672, URL: https://europepmc.org/backend/ptpmcrender.fcgi?accid=PMC106213&blobtype=pdf.
Laura Pérez-Través et al., "Evaluation of different genetic procedures for the generation of artificial hybrids ingenus for winemaking", International Journal of Food Microbiology, Elsevier BV, NL, vol. 156, No. 2, doi:10.1016/J.IJFOODMICRO.2012.03.008, ISSN 0168-1605, (Mar. 7, 2012), pp. 102-111, (Mar. 14, 2012).
De Barros Lopes, M, "Evidence for multiple interspecific hybridization in *Saccharomyces sensu* stricto species", Fems Yeast Research, (Dec. 5, 2001), vol. 1, pp. 323-331.
International Search Report & Written Opinion issued in corresponding application No. PCT/NL2019/050279 dated Sep. 17, 2019, 12 pages.
Katsuragi, et al. "Selection of hybrids from protoplast fusion of yeasts by double fluorescence labelling and automatic cell sorting". Letters in Applied Microbiology, 1994, 19, 92-92, 3 pages.
Alani et al., "Analysis of Wild-Type and rad50 Mutants of Yeast Suggests an Intimate Relationship between Meiotic Chromosome Synapsis and Recombination," Cell, vol. 61, May 4, 1990, pp. 419-436, 18 pages.
Alexander et al., "Efficient engineering of marker-free synthetic allotetraploids of *Saccharomyces*," Fungal Genetics and Biology, 89, 2016, pp. 10-17, 8 pages.

(Continued)

*Primary Examiner* — Brian Gangle
(74) *Attorney, Agent, or Firm* — Banner & Witcoff, Ltd.

(57) ABSTRACT

The invention relates to methods for identifying a hybrid organism, based on staining of parent cells with a dye, preferably a fluorescent dye. A preferred dye is a succinimidyl ester-coupled dye. The invention further relates to the resulting hybrid organism, preferably an interspecies hybrid organism, that is labelled with a dye.

10 Claims, 11 Drawing Sheets

Figure 1:
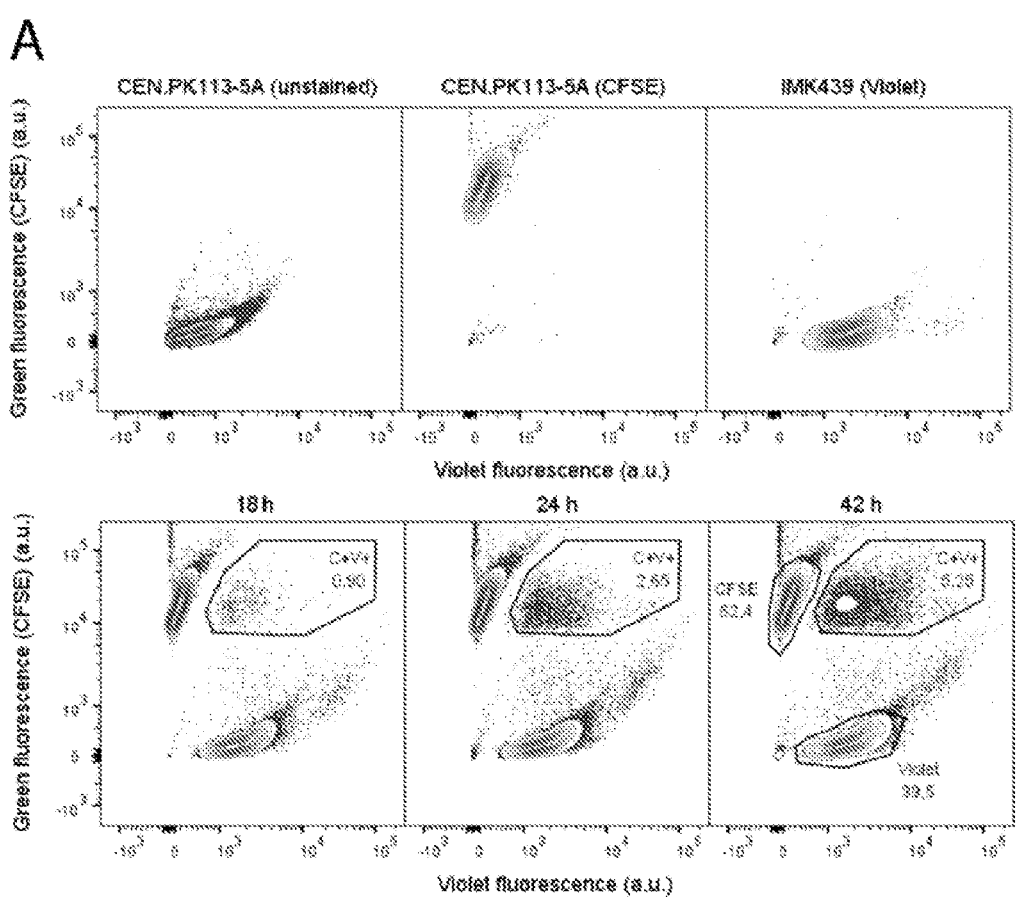
Figure 1:
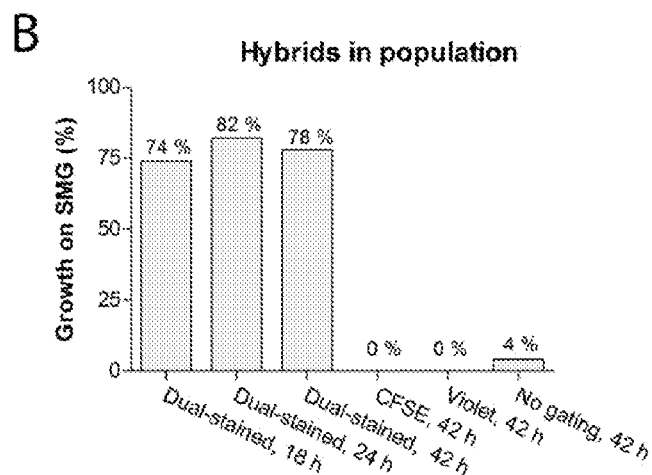
Figure 1:
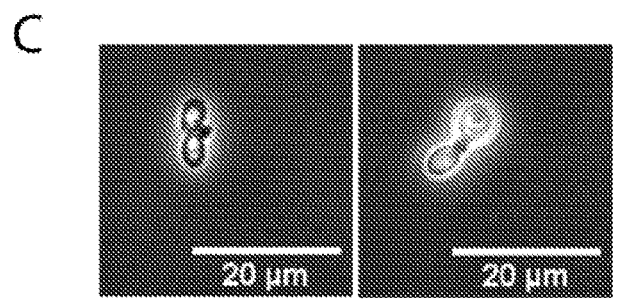
Figure 1:
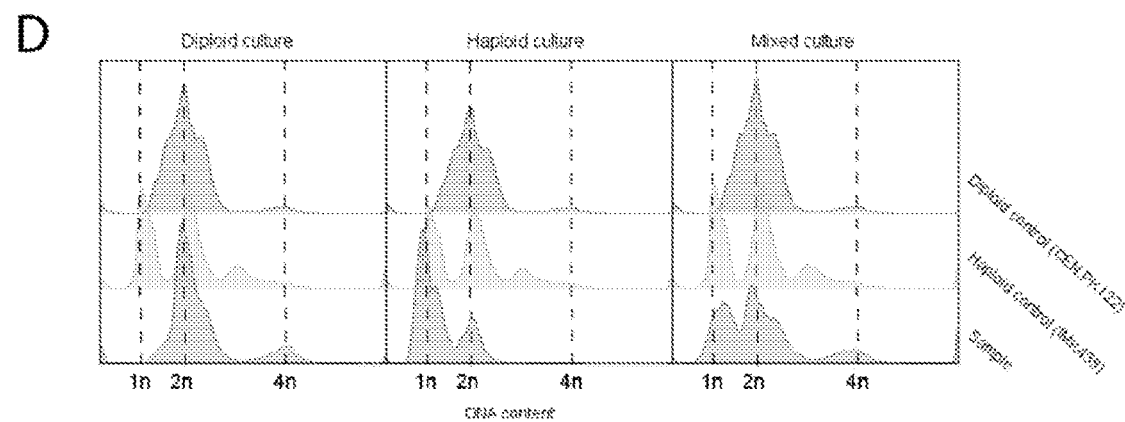

Specification includes a Sequence Listing.

(56) References Cited

OTHER PUBLICATIONS

Bahalul et al., "Ether-zymolyase ascospore isolation procedure: an efficient protocol for ascospores isolation in *Saccharomyces cerevisiae* yeast," Yeast, Jul. 14, 2010, pp. 999-1003, 5 pages.

Balat, "Production of bioethanol from lignocellulosic materials via the biochemical pathway: A review," Energy Conversion and Management, 52, 2011, pp. 858-875, 18 pages.

Beckman et al., "Cultural Techniques and Conditions Influencing Growth and Sporulation of Cercospora zeae-maydis and Lesion Development in Corn," Ecology and Epidemiology, vol. 73, No. 2, 1983, pp. 286-289, 4 pages.

Bellon et al., "Newly generated interspecific wine yeast hybrids introduce flavour and aroma diversity to wines," Applied Microbiology and Biotechnology, May 2011, 11 pages.

Bellon et al., "Introducing a New Breed of Wine Yeast: Interspecific Hybridisation between a Commercial *Saccharomyces cerevisiae* Wine Yeast and *Saccharomyces mikatae*," PLOS One, vol. 8, Issue 4, Apr. 2013, 14 pages.

Bellon et al., "Designing and creating *Saccharomyces* interspecific hybrids for improved, industry relevant, phenotypes," Applied Microbiology and Biotechnology, 99, 2015, pp. 8597-8609, 13 pages.

Bing et al., "Evidence for a Far East Asian origin of lager beer yeast," Current Biology, vol. 24, No. 10, 2 pages.

Bizaj et al., "A breeding strategy to harness flavor diversity of *Saccharomyces* interspecific hybrids and minimize hydrogen sulfide production," FEMS Yeast Research, 12, 2012, pp. 456-465, 10 pages.

Boynton et al., "The ecology and evolution of non-domesticated *Saccharomyces* species," Yeast, 31, Oct. 23, 2014, pp. 449-462, 14 pages.

Cheng et al., "Controlling gene expression in yeast by inducible site-specific recombination," Nucleic Acids Research, vol. 28, No. 24, 2000, 6 pages.

Coloretti et al., "Characterization of flocculent *Saccharomyces* interspecific hybrids for the production of sparkling wines," Food Microbiology, 23, 2006, pp. 672-676, 5 pages.

Da Silva et al., "Hybridization within *Saccharomyces* Genus Results in Homoeostasis and Phenotypic Novelty in Winemaking Conditions," PLOS One, 10(5), May 6, 2015, 24 pages.

Dube et al., "Mathematical Analysis of Copy Number Variation in a DNA Sample Using Digital PCR on a Nanofluidic Device," PLOS One, vol. 3, Issue 8, Aug. 2008, 9 pages.

Dunn et al., "Analysis of the *Saccharomyces cerevisiae* pan-genome reveals a pool of copy number variants distributed in diverse yeast strains from differing industrial environments," Genome Research, 22, 2012, pp. 908-924, 18 pages.

Entian et al., "25 Yeast Genetic Strain and Plasmid Collections," Methods in Microbiology, vol. 36, 2007, pp. 629-666, 38 pages.

Fernandez-Gonzalez et al., "Study of *Saccharomyces cerevisiae* Wine Strains for Breeding Through Fermentation Efficiency and Tetrad Analysis," Current Microbiology, 70, 2015, pp. 441-449, 9 pages.

Gonzalez et al., "Natural hybrids from*Saccharomyces cerevisiae* , *Saccharomyces bayanus* and*Saccharomyces kudriavzevii* in wine fermentations," FEMS Yeast Research, 6, 2006, pp. 1221-1234, 14 pages.

Gonzalez-Ramos et al., "Genome-scale analyses of butanol tolerance in *Saccharomyces cerevisiae* reveal an essential role of protein degradation," Biotechnology for Biofuels, 6:48, 2013, 18 pages.

Gorter De Vries et al., "CRISPR-Cas9 mediated gene deletions in lager yeast *Saccharomyces pastorianus*," Microbial Cell Factories, 16: 222, 2017, 18 pages.

Greig et al., "Epistasis and hybrid sterility in *Saccharomyces*," Proc. R. Soc. Lond. B (2002) 269, pp. 1167-1171, 5 pages.

Gunge et al., "Genetic Mechanisms of Rare Matings of the Yeast *Saccharomyces cerevisiae* Heterozygous for Mating Type," Genetics, 70, Jan. 1972, pp. 41-58, 18 pages.

Haase et al., "Improved Flow Cytometric Analysis of the Budding Yeast Cell Cycle," Cell Cycle, 1:2, Mar. 2002, pp. 117-121, 6 pages.

Hebly et al., "*S. cerevisiae* x S. eubayanus interspecific hybrid, the best of both worlds and beyond," FEMS Yeast Research, vol. 15, No. 3, 2015, 14 pages.

Herman et al., "Yeast spore germination: a requirement for Ras protein activity during re-entry into the cell cycle," The EMBO Journal, vol. 16, No. 20, 1997, pp. 6171-6181, 11 pages.

Hierskowitz, "Life Cycle of the Budding Yeast *Saccharomyces cerevisiae*," Microbiological Reviews, vol. 52, No. 4, Dec. 1988, pp. 536-553, 18 pages.

Hittinger, "*Saccharomyces* diversity and evolution: a budding model genus," Trends in Genetics, vol. 29, No. 5, May 2013, pp. 309-317, 9 pages.

Hou et al., "Chromosomal Rearrangements as a Major Mechanism in the Onset of Reproductive Isolation in *Saccharomyces cerevisiae*," Current Biology, 24, May 19, 2014, pp. 1153-1159, 7 pages.

Jansen et al., "*Saccharomyces cerevisiae* strains for second-generation ethanol production: from academic exploration to industrial implementation," FEMS Yeast Research, 17, 2017, 20 pages.

Kisaka et al., "Intergeneric somatic hybridization of rice (*Oryza sativa* L.) and barley (*Hordeum vulgare* L.) by protoplast fusion," Plant Cell Reports, 17, 1998, pp. 362-367, 6 pages.

Krogerus et al., "New lager yeast strains generated by interspecific hybridization," J Ind Microbiol Biotechnol, 42, 2015, pp. 769-778, 10 pages.

Krogerus et al., "Ploidy influences the functional attributes of de novo lager yeast hybrids," Appl Microbiol Biotechnol, 2016, 100, pp. 7203-7222, 20 pages.

Krogerus et al., "Inheritance of brewing-relevant phenotypes in constructed *Saccharomyces cerevisiae* x *Saccharomyces eubayanus* hybrids," Microbial Cell Factories, 2017, 16:66, 22 pages.

Krogerus et al., "Novel brewing yeast hybrids: creation and application," Appl Microbiol Biotechnol, 2017, 101, pp. 65-78, 14 pages.

Libkind et al., "Microbe domestication and the identification of the wild genetic stock of lager-brewing yeast," PNAS, vol. 108, No. 35, Aug. 30, 2011, pp. 14539-14544, 6 pages.

Lipke et al., "Sexual Agglutination in Budding Yeasts: Structure, Function, and Regulation of Adhesion Glycoproteins," Microbiological Reviews, vol. 56, No. 1, Mar. 1992, pp. 180-194, 15 pages.

Lopandic et al., "Genotypic and phenotypic evolution of yeast interspecies hybrids during high-sugar fermentation," Appl Microbiol Biotechnol, 2016, 100, pp. 6331-6343, 14 pages.

Magalhaes et al., "Improved cider fermentation performance and quality with newly generated *Saccharomyces cerevisiae* x *Saccharomyces eubayanus* hybrids," J Ind Microbiol Biotechnol, 2017, 44, pp. 1203-1213, 11 pages.

Marsit et al., "Diversity and adaptive evolution of *Saccharomyces* wine yeast: a review," FEMS Yeast Research, 15, 2015, 12 pages.

Matsumoto et al., "Somatic hybridization by electrofusion of banana protoplasts," Euphytica, 125, 2002, pp. 317-324, 8 pages.

Mertens et al., "A Large Set of Newly Created Interspecific Saccharomyces Hybrids Increases Aromatic Diversity in Lager Beers," Applied and Environmental Microbiology, vol. 81, No. 23, Dec. 2015, pp. 8202-8214, 13 pages.

Morales et al., "Evolutionary Role of Interspecies Hybridization and Genetic Exchanges in Yeasts," Microbiology and Molecular Biology Reviews, vol. 76, No. 4, Dec. 2012, pp. 721-739, 19 pages.

Muir et al., "A multiplex set of species-specific primers for rapid identification of members of the genus *Saccharomyces*," FEMS Yeast Research, 11, 2011, pp. 552-563, 12 pages.

Naseeb et al., "*Saccharomyces jurei* sp. nov., isolation and genetic identification of a novel yeast species from Quercus robur," International Journal of Systematic and Evolutionary Microbiology, 2017, 67, pp. 2046-2052, 7 pages.

Naumova et al., "Genetic diversity study of the yeast *Saccharomyces bayanus* var. uvarum reveals introgressed subtelomeric *Saccharomyces cerevisiae* genes," Research in Microbiology, 162, 2011, pp. 204-213, 10 pages.

Nielsen, "Production of biopharmaceutical proteins by yeast," Bioengineered, 4:4, 2013, pp. 207-211, 6 pages.

Nikulin et al., "Alternative *Saccharomyces* interspecies hybrid combinations and their potential for low-temperature wort fermentation," Yeast, 2018, 35, pp. 113-127, 15 pages.

(56) References Cited

OTHER PUBLICATIONS

Pengelly et al., "Rapid identification of *Saccharomyces eubayanus* and its hybrids," FEMS Yeast Research, 2013, 13, pp. 156-161, 6 pages.

Peris et al., "Hybridization and adaptive evolution of diverse *Saccharomyces* species for cellulosic biofuel production," Biotechnology for Biofuels, 2017, 10:78, 19 pages.

Piotrowski et al., "Different selective pressures lead to different genomic outcomes as newly-formed hybrid yeasts evolve," BMC Evolutionary Biology, 2012, 12:46, 17 pages.

Scannell et al., "The Awesome Power of Yeast Evolutionary Genetics: New Genome Sequences and Strain Resources for the *Saccharomyces sensu stricto* Genus," Genes | Genomes | Genetics, vol. 1, Jun. 2011, pp. 11-25, 15 pages.

Schindelin et al., "Fiji—an Open Source platform for biological image analysis," Nat Methods, 9(7), Dec. 7, 2013, 15 pages.

Shapira et al., "Extensive heterosis in growth of yeast hybrids is explained by a combination of genetic models," Heredity, 2014, 113, pp. 316-326, 11 pages.

Sherman, "Respiration-Deficient Mutants of Yeast. I. Genetics," Genetics, 48, Mar. 1963, pp. 375-385, 11 pages.

Steensels et al., "Improving industrial yeast strains: exploiting natural and artificial diversity," FEMS Microbiology Reviews, 38, 2014, pp. 947-995, 49 pages.

Steensels et al., "Large-Scale Selection and Breeding to Generate Industrial Yeasts with Superior Aroma Production," Applied and Environmental Microbiology, vol. 80, No. 22, Nov. 2014, pp. 6965-6975, 11 pages.

Stefanini et al., "Social wasps are a *Saccharomyces* mating nest," PNAS, vol. 113, No. 8, Feb. 23, 2016, pp. 2247-2251, 5 pages.

Wang et al., "The sporulation of the green alga Ulva prolifera is controlled by changes in photosynthetic electron transport chain," Scientific Reports, www.nature.com/scientificreports/, Apr. 22, 2016, 9 pages.

Wunderlich et al., "Consumer Perception of Genetically Modified Organisms and Sources of Information," American Society for Nutrition, Adv. Nutr., 2015, 6, pp. 842-851, 10 pages.

Yeast cell fusion and its utilization, Journal of the Brewing Society of Japan, 1984, vol. 79, No. 4, pp. 210-215.

Yeast Growth, Journal of the Brewing Society of Japan, 1974, vol. 69, No. 1, pp. 21-24.

B

C

D

IDENTIFICATION OF RARE PRODUCTS OF CROSSING ORGANISMS

The invention relates to the field of organisms, especially of microorganisms such as yeast. More specifically, the invention relates to the generation and identification of hybrid organisms, especially of interspecies hybrids such as generated by rare mating events.

Yeasts of the *Saccharomyces* genus are widely used in a variety of biotechnological industries including beer brewing [Krogerus et al., 2017. Appl Microbiol Biotechnol 101: 65-78], winemaking [Marsit and Dequin, 2015. FEMS Yeast Res 15: 72], production of biopharmaceutical proteins [Nielsen, 2013. Bioengin 4: 207-211] and the synthesis of first- and second generation biofuels [Balat, 2011. Energy Cony Management 52: 858-875; Jansen et al., 2017. FEMS Yeast Res 17: fox044]. The *Saccharomyces sensu stricto* complex encompasses nine different species: *Saccharomyces cerevisiae, S. paradoxus, S. cariocanus, S. uvarum, S. mikatae, S. kudriauzevii, S. arboricola, S. eubayanus* and the recently discovered *S. jurei* [Hittinger, 2013. Trends Genet 29: 309-317; Naseeb et al., 2017. Int J Syst Evol Microbiol 67: 2046-2052]. There is a postzygotic barrier between the different *Saccharomyces* species, meaning that interspecies mating between the species is possible but yields sterile offspring [Greig et al., 2002. Proc Royal Society London B: Biological Sciences 269: 1167-1171; Hou et al., 2014. Current Biol 24: 1153-1159]. Although some interspecies hybrids have been found in diverse natural contexts, such as in the guts of wasps [Stefanini et al., 2016. PNAS 113: 2247-2251], *Saccharomyces* hybrids are most commonly found in domesticated environments and are used in various industrial fermentation processes [Boynton and Greig, 2014. Yeast, 31: 449-462; Gorter de Vries et al., 2017. Applied Environm Microbiol 83: e03206-16]. For instance, lager brewing is performed with *S. pastorianus*, a hybrid between *S. cerevisiae* and *S. eubayanus* [Libkind et al., 2011. PNAS 108: 14539-14544], which combines the fermentative capacity and sugar utilisation of *S. cerevisiae* with the cryotolerance of *S. eubayanus* [Hebly et al., 2015. FEMS Yeast Res 15: fov005]. Various double and triple hybrids between *S. cerevisiae, S. kudriauzevii* and *S. uvarum* have been isolated from wine fermentations and appear to play an important role in aroma production [Gonzalez et al., 2006. FEMS Yeast Res 6: 1221-1234]. Another important contribution of hybridization to the genetic variation of domesticated *Saccharomyces* strains are genetic introgressions, caused by interspecies hybridization followed by rounds of backcrossing with one of the parental strains. Such introgressions are common in many domesticated *Saccharomyces* strains and contribute to the distinct phenotypes of for instance cider fermenting *S. uvarum* strains and wine fermenting *S. cerevisiae* strains [Naumova et al., 2011. Research Microbiol 162: 204-213; Dunn et al., 2012. Genome Res 22: 908-924].

The combination of two or more *Saccharomyces* genomes in a hybrid commonly results in synergistic effects, a phenomenon called 'heterosis' or 'hybrid vigor', which enables the hybrid to perform better than either of its parents in specific environments [Shapira et al., 2014. Heredity 113: 316]. Therefore, targeted hybridisation of *Saccharomyces* yeasts is commonly used to generate strains with new or improved phenotypes for industrial applications. For instance, laboratory-made *S. cerevisiae*×*S. eubayanus* hybrids showed higher cold tolerance and oligosaccharide consumption [Hebly et al., 2015. FEMS Yeast Res 15: fov005], different flavour profiles [Steensels et al., 2014. Applied Environment Microbiol 80: 6965-6975], higher fermentation rates and higher ethanol titers [Krogerus et al., 2015. J Industrial Microbiol & Biotechnol 42: 769-778] than their parental strains. In addition to naturally occurring hybrids, novel interspecies hybrids that have not been isolated in nature were created, such as *S. cerevisiae*×*S. paradoxus* hybrids [Bellon et al., 2011. Appl Microbiol and Biotechnol 91: 603-612], *S. cerevisiae*×*S. mikatae* hybrids [Bellon et al., 2013. PLoS One 8: e62053; Nikulin et al., 2018. Yeast 35: 113-127], *S. cerevisiae*×*S. arboricola* hybrids [Nikulin et al., 2018. Yeast 35: 113-127] and *S. cerevisiae*×*S. uvarum* hybrids [Bellon et al., 2015. Appl Microbiol Biotechnol 99: 8597-8609; Lopandic et al., 2016. Appl Microbiol Biotechnol 100: 6331-6343]. These hybrids combined properties of both parental strains, resulting in novel phenotypic diversity which could be exploited for applications ranging from the fermented beverage industry to the production of biofuels [Penis et al., 2017. Biotechnol Biofuels 10: 78].

Heterosis is a complex phenomenon which is not yet fully understood; it is most likely caused by a combination of multiple factors, including the amount of chromosomal copy numbers [Gorter de Vries et al., 2017. Applied Environm Microbiol 83: e03206-16; Krogerus et al., 2016. Appl Microbiol Biotechnol 100: 7203-7222], interactions between different dominant and recessive alleles and epistatic interactions [Shapira et al., 2014. Heredity 113: 316]. The resulting phenotype is not always ambiguous: dominant and usually more complex phenotypes such as cryotolerance or flocculation are usually completely inherited from one of the parental strains [Hebly et al., 2015. FEMS Yeast Res 15: fov005; Coloretti et al., 2006. Food Microbiol 23: 672-676], while for flavour compounds and other secondary metabolites the hybrids generally produce concentrations around the average of the concentrations produced by their parental strains [Krogerus et al., 2015. J Industrial Microbiol & Biotechnol 42: 769-778; Bellon et al., 2011. Appl Microbiol and Biotechnol 91: 603-612]. Heterosis is not only dependent on the parental species used for interspecies hybridization, but also on the specific strains used, making it even more difficult to predict the phenotype of an outcross. For example, laboratory-made *S. cerevisiae*×*S. eubayanus* hybrids of different parental strains show distinctive fermentation characteristics and flavour profiles [Krogerus et al., 2017. Microbial Cell Factories 16: 66; Mertens et al., 2015. Appl Environm Microbiol 81: 8202-8214]. Consequently, the generation of industrially relevant hybrids relies on a trial-and-error process in which as many hybrids as possible have to be generated and screened in order to find a strain with optimal characteristics [Steensels et al., 2014. FEMS Microbiol Reviews 38: 947-995]. Therefore, the development of new efficient high-throughput screening strategies could simplify and streamline the generation of hybrids with potential for industrial applications.

Interspecies hybrids of species without a prezygotic barrier can be obtained analogously to intraspecific mating: hybrids are formed by either mating haploid strains of opposite mating type, or by rare mating between strains which do not have opposite mating types that have undergone spontaneous loss of heterozygosity in the mating type locus [Steensels et al., 2014. FEMS Microbiol Reviews 38: 947-995]. Interspecies hybridization has a relatively low occurrence rate; hybridization frequencies are reported to range from 1.5-3.6% for spore-to-spore mating [Krogerus et al., 2016. Appl Microbiol Biotechnol 100: 7203-7222; Mertens et al., 2015. Appl Environment Microbiol 81: 8202-8214] to frequencies as low as $1 \times 10^{-6}$ to $1 \times 10^{-7}$ for rare mating [Krogerus et al., 2017. Microbial Cell Factories 16: 66; Gunge and Nakatomi, 1972. Genetics 70: 41-58]. Because interspecies mating occurs in such low frequencies, the vast majority of mating cultures consists of unmated parental cells and mated non-hybrid cells, making it challenging to isolate the desired hybrids. The efficiency of interspecies hybridization can be improved by various methods such as expression of an inducible HO-endonuclease increasing the occurrence of mating-type switches which enable mating [Alexander et al., 2016. Fungal Genet Biol 89: 10-17]. If hybrids are obtained in the mating culture, they can be isolated from mating cultures by growth under conditions favouring hybridized cells over non-hybrid cells. This can be achieved by exploiting complementary phenotypes of both parental strains, for example, by crossing S. cerevisiae strains able to grow at 37° C. with other Saccharomyces species that can ferment certain sugars more efficiently or grow at low pH [Bizaj et al., 2012. FEMS Yeast Res 12: 456-465]. Such selection can be greatly simplified by the introduction of selectable phenotypes in the parental strains which can easily be selected for or against such as auxotrophies or resistances. While introduction of such markers is readily achieved using genetic modification [Hebly et al., 2015. FEMS Yeast Res 15: fov005; Piotrowski et al., 2012. BMC Evolut Biol 12: 46; da Silva et al., 2015. PloS one 10: e0123834], this process can be time-consuming and is rarely used in food-related industrial applications, due to customer acceptance and legislation issues [Wunderlich and Gatto, 2015. Advances Nutrition 6: 842-851]. Consequently, the construction of interspecies hybrids mainly relies on crossing strains with pre-existing complementary auxotrophies and selecting their hybrids on a selective medium. Auxotrophies can either occur naturally [Magalhães et al., 2017. J Indus Microbiol Biotechnol 44: 1203-1213; Fernandez-Gonzalez et al., 2015. Current Microbiol 70: 441-449] or can be obtained without any genetic engineering techniques by laboratory evolution under conditions favouring auxotrophic strains [Krogerus et al., 2015. J Industrial Microbiol & Biotechnol 42: 769-778; Perez-Través et al., 2012. Int J Food Microbiol 156: 102-111; Scannell et al., 2011. Genes Genomes Genet 1: 11-25], making it a reliable, GMO-free technique. However, obtaining the auxotrophic mutants required for a cross is time- and labour-intensive, as auxotrophies have to be obtained for each parental strain and the occurrence frequency of auxotrophic mutations is low [Alexander et al., 2016. Fungal Genet Biol 89: 10-17]. Furthermore, many industrially relevant Saccharomyces strains are polyploid or aneuploid, which complicates the generation of auxotrophic mutants [Gorter de Vries et al., 2017. Applied Environm Microbiol 83: e03206-16; Pérez-Través et al., 2012. Int J Food Microbiol 156: 102-111; Bell, 1998. Appl Environment Microbiol 64: 1669-1672].

Overall, a high-throughput method to select for hybrids from crosses between any strain without prior genetic modification or lengthy procedures would greatly simplify interspecies mating in general, and the generation of industrially relevant hybrid Saccharomyces strains in particular. Fluorescent dyes offer an elegant solution here, as fluorophores can be used to label any cell by a simple and short procedure without a need for genetic engineering. Preferred dyes have limited effect on viability. When using different fluorophores for both parental strains, hybrid cells would be identifiable as double-stained and could be isolated using fluorescent-activated cell sorting (FACS). In 1994, protoplasts of Saccharomyces cerevisiae and Saccharomycopsis fibulgera strains were fluorescently labelled, fused and dual-stained cells were sorted by FACS [Katsuragi et al., 1994. Letters Appl Microbiol 19: 92-94]. Using this technique, 3'600 viable potential fusants were sorted from a pool of 9'800'000 protoplasts, of which at least one was confirmed to be a hybrid. However, as protoplast fusion is considered a GMO technique [Krogerus et al., 2017. Appl Microbiol Biotechnol 101: 65-78], its application is precluded in the food- and beverage industry.

In 1998, two heterothallic haploid S. cerevisiae yeasts were labelled with different fluorescent stains and subsequently mated with each other and enriched for dual-stained cells using FACS [Bell, 1998. Appl Environment Microbiol 64: 1669-1672]. In two successive sorting rounds, the culture was enriched from 33% mated cells to 96% mated cells, a less than threefold enrichment. The authors applied the same method to mate a diploid industrial S. cerevisiae strain and haploid S. cerevisiae strain with auxotrophies for histidine and tryptophan and with an integrated LacZ marker. After two successive sorting rounds from a pool containing more than $2 \times 10^6$ cells, three out of 50 dual-stained cells were identified as hybrids by their prototrophy for histidine and tryptophan, LacZ activity and PCR fingerprint, although the data is not shown. Furthermore, observation of sorted cells under the microscope indicated the sorted population consisted of cell clusters of mated and non-mated parental cells. Therefore it is not excluded that the double stained cells are not single cells but clusters of parental cells that together have a PCR fingerprint consistent with a hybrid or have hybridized under the pressure of selective medium. The inability to discriminate between single mated cells and cell clusters may explain the exceptional frequency of 33% mated cells prior to sorting and may have resulted in mixed populations in the sorted cells. While these mixed populations are not an issue when strains with markers are used, it becomes impossible to identify hybrid cells when marker-free strains are used. As the initial frequency of rare mating events prior to sorting is unknown, enrichment factors cannot be determined. Although intraspecific mating has a higher occurrence rate than interspecies hybridization [Morales and Dujon, 2012. Microbiol Molec Biol Reviews 76: 721-739], this method for marker-free intraspecific mating could yield interspecies hybrids if a high enough enrichment factor can be achieved.

BRIEF DESCRIPTION OF THE INVENTION

The invention provides a method for identifying a hybrid organism, comprising providing cells from a first and second parent organism, whereby the first and second organism are mating-compatible, whereby the first parent organism differs from the second parent organism, whereby said first parent organism, but not said second parent organism, carries an auxothrophy marker, labelling cells from the second parent organism with a fluorescent dye; hybridizing cells from the first parent with labelled cells from the second parent at a temperature that is at least 5° C. below the optimal growth temperature of the first and/or the second parent organism; and identifying a hybrid organism as an auxotrohophic, labelled cell.

The invention further provides a method for identifying a hybrid organism, comprising labelling cells from a first parent organism with dye A; labelling cells from a second parent organism with dye B; whereby the first parent organism is identical to, or differs from the second parent organism, whereby the first and second organism are mating-compatible, whereby dye A and dye B are fluorescent dyes and dye A differs from dye B, and whereby cells labelled with dye A can be discriminated from cells labelled with dye B; hybridizing labelled cells from the first parent with labelled cells from the second parent at a temperature that is at least 5° C. below the optimal growth temperature of the first and/or the second parent organism; and identifying a hybrid organism as a dual labelled cell.

Said cells from the first and/or second parent organism are preferably gametes or spores. More specifically, the cells from the first and/or from the second parent organism are gametes or spores that are labelled after germination. Especially in yeast, gametes, also termed haploid spores, may enter the mitotic cell cycle under appropriate conditions. It was found that labelling of gametes, especially haploid spores, was dramatically improved if the cells were labelled after germination.

Said cells from the first or from the second parent organism are preferably polyploid, such as diploid, triploid, tetraploid, pentaploid, or aneuploid, preferably diploid.

The first and second parent organisms are preferably microorganisms, more preferably yeasts, preferably *Saccharomyces sensu stricto* yeasts.

In a preferred method of the invention, the first and second organisms are different species and the resulting hybrid is an interspecies hybrid.

'The identification of a hybrid organism in a method of the invention is preferably performed by fluorescence activated cell sorting (FACS).

In a preferred method of the invention, identification of a dual labelled cell is followed by isolation of the dual labelled cell from singular labelled cells. Said isolated dual labelled cell is preferably subjected to a second round of identifying a hybrid organism as a dual labelled cell and isolating the dual labelled cell from singular labelled cells. Said second round may be performed after culturing the isolated dual labelled cell.

It is preferred that at least one of fluorescent dyes A and B is a succinimidyl ester-coupled dye, preferably both fluorescent dyes A and B are succinimidyl ester-coupled dyes.

The invention further provides a hybrid organism that is labelled with dye A and dye B. Said hybrid organism preferably is an interspecies hybrid. Said hybrid organism preferably is a yeast, more preferably a progeny of a cross between a *Saccharomyces cerevisiae* parent strain and a *S. eubayanus* parent strain.

FIGURE LEGENDS

FIG. 1: Analysis and validation of intraspecific mating of CEN.PK113-5A MATα URA3 his3-Δ1 leu2-3, 112 trp1-289)×IMK439 (MATαHIS3 TRP1 LEU2 ura3Δ::KanMX). (A) Contour plots of fluorescence intensities of unstained CEN.PK113-5A, CEN.PK113-5A stained with CFSE and IMK439 stained with Violet prior to mating and after 18, 24 and 42 h of mating. 100'000 cells were analysed per plot, the green and violet fluorescence intensity of each cell is show. The gated areas were used for sorting cells, event rates of each gate are indicated as a percentage. (B) Percentage of cells able to grow in synthetic minimal medium in different populations sorted by FACS. The amount of mated cells is determined as the fraction viable cells grown on YPD that are also able to grow on synthetic minimal (SM) medium. (C) Microscope image (400×) of zygotic cells sorted from the dual-stained population (C+V+). Up to 10% of sorted dual-stained cells had this physiology, while the rest had a normal budding physiology. (D) Ploidy assessment of CEN.PK113-5A×IMK439 crosses. DNA content of CEN.PK122 (diploid), IMK439 (haploid), and putative mated cells was measured by DNA staining and flow cytometry. Depicted are three representative graphs of (from left to right) a colony with diploid genome content, haploid genome content and a mix of both.

Figure 2:
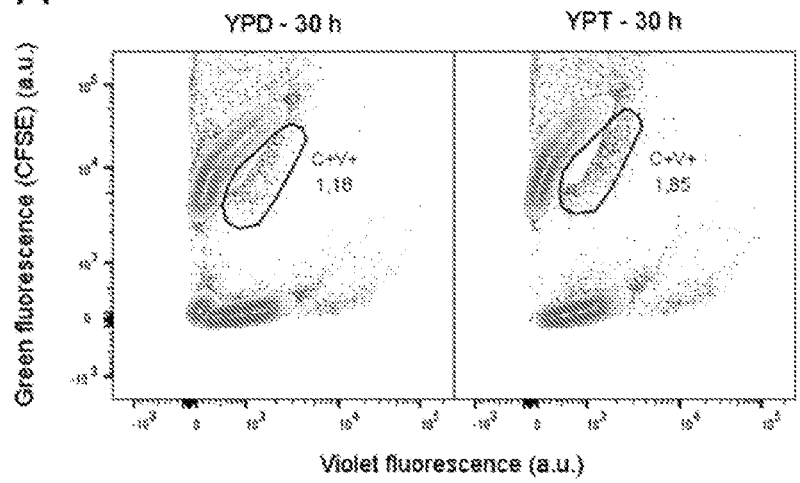
Figure 2:
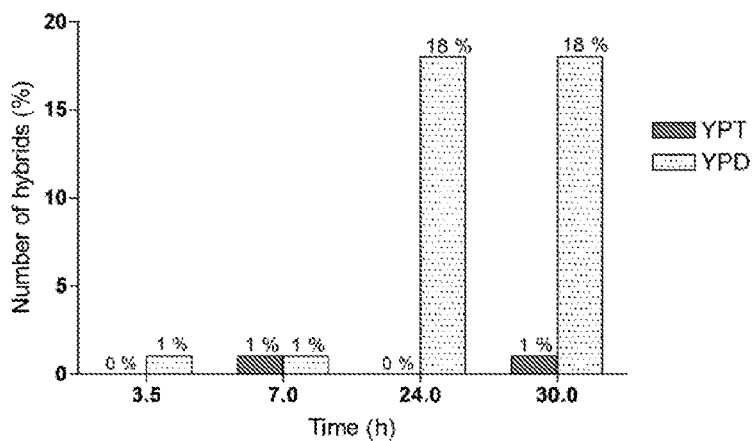
Figure 2:
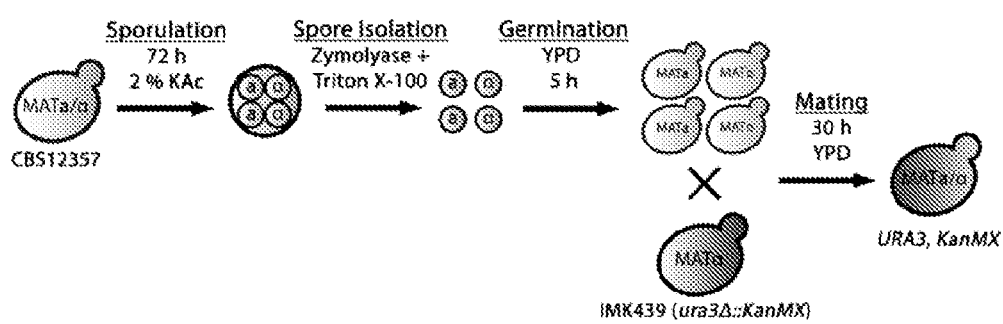

FIG. 2. Optimization of mating between *S. eubayanus* and *S. cerevisiae* and isolation of putative hybrids. (A) Contour plots of fluorescence intensities of stained CBS12357 and IMK439 cells after 30 h of mating on YPD and YPT. 100'000 cells were analysed per plot, the green and violet fluorescence intensity of each cell is shown. The gated areas were used for sorting cells, event rates of each gate are indicated as a percentage. (B) Percentages of hybrids present in the dual stained population after 3.5, 7, 24 and 30 h of incubation on YPT and YPD. The percentage is calculated as the amount of single-cell sorted colonies able to grow on SM +G418. (C) Overview of the optimized parameters in the protocol for spore-to-cell interspecies hybridization of *S. eubayanus* CBS12357 and *S. cerevisiae* IMK439.

Figure 3:
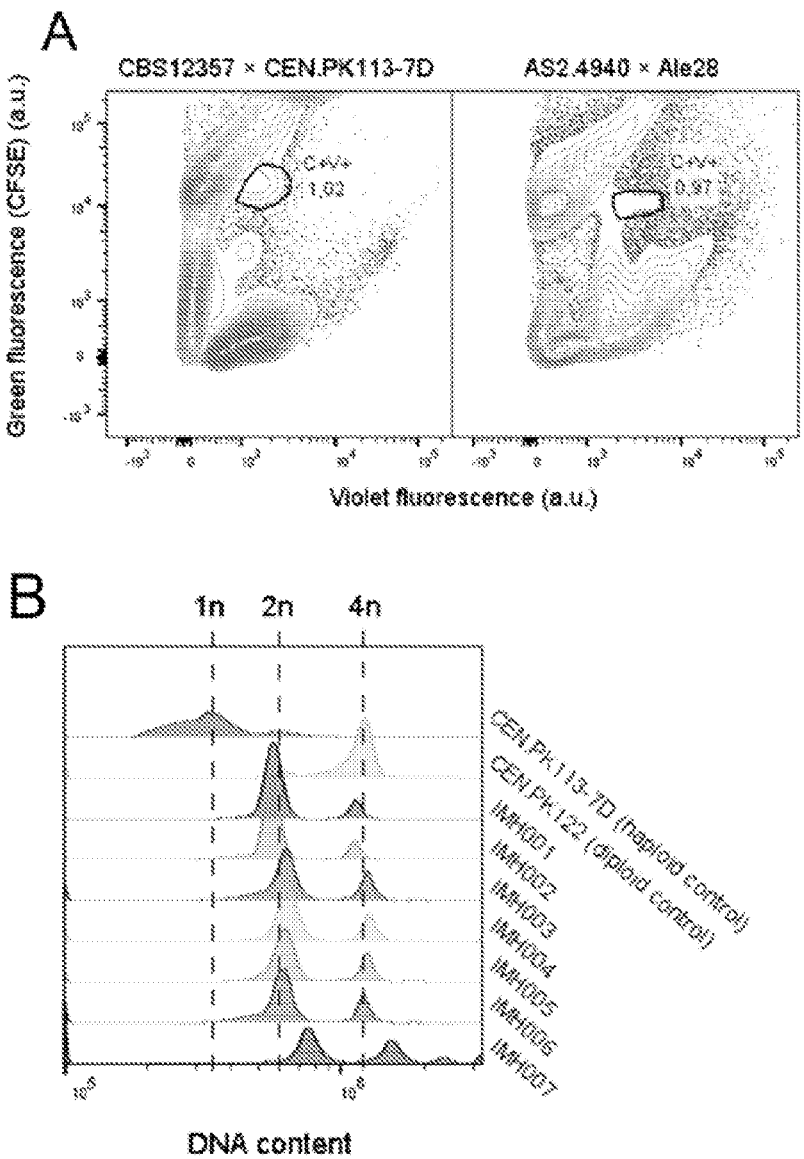
Figure 3:
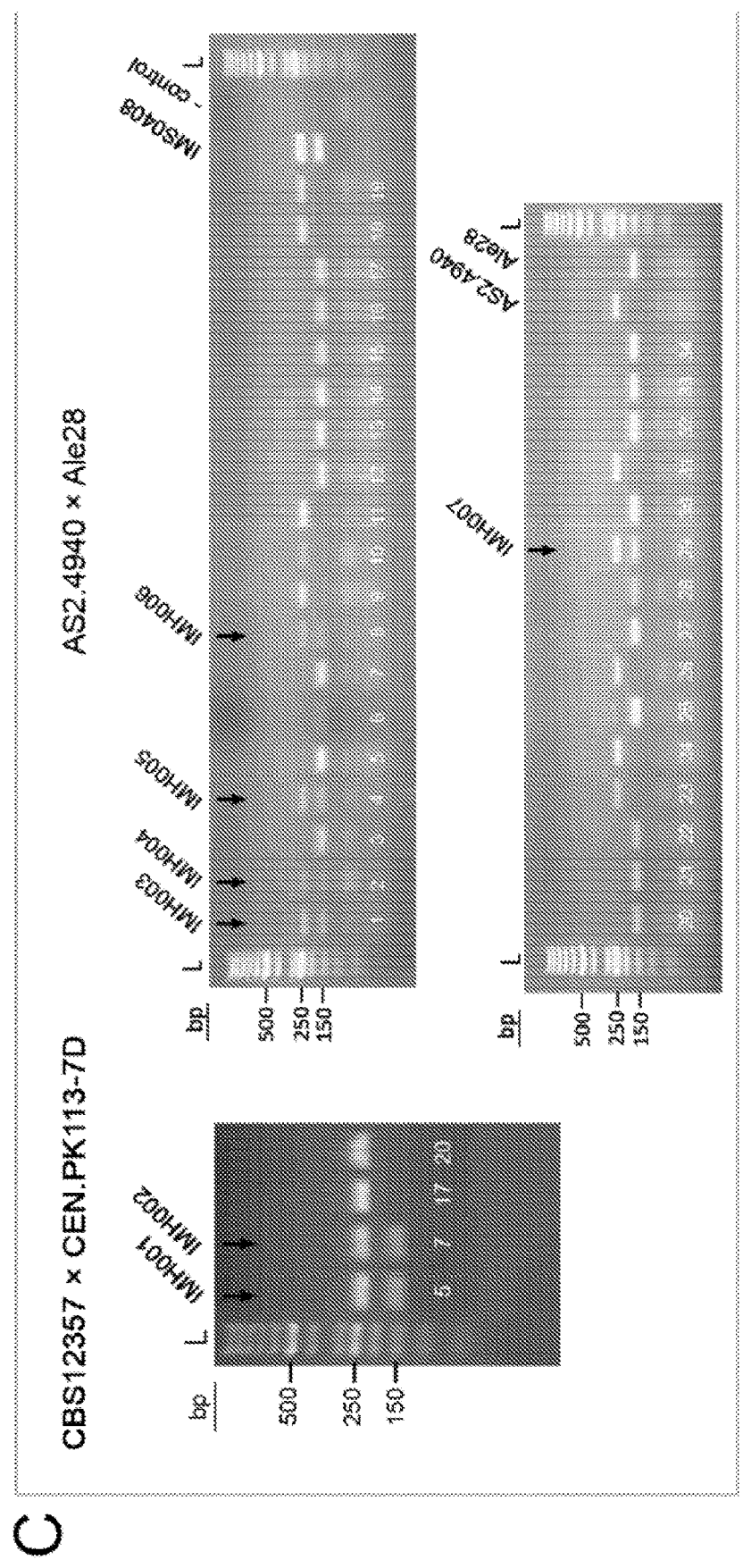

FIG. 3. Analysis and validation of marker-free interspecies mating of CBS12357 (*S. eubayanus*, sporulated)×CEN.PK113-7D (MATa) and AS2.4940 (*S. eubayanus*, sporulated)×Ale28 (*S. cerevisiae*, sporulated). (A) Contour plots of fluorescence intensities measured in mating cultures between CBS12357 (CFSE stained)×CEN.PK113-7D (Violet stained) and AS2.4940 (CFSE stained)×Ale28 (Violet stained). 100'000 cells were analysed per plot, the green and violet fluorescence intensity of each population are shown. The gated areas were used for sorting cells, event rates of each gate are indicated in the figure as a percentage. (B) Ploidy assessment of constructed marker-free hybrids. DNA content of CEN.PK122 (diploid, red), CEN.PK113-7D (haploid, green), and PCR-confirmed hybrids (coloured) was measured by DNA staining and flow cytometry. (C) Multiplex colony PCR for confirmation of the presence of *S. eubayanus* and *S. cerevisiae* marker genes in single-cell isolates of the dual-stained populations from CBS12357×CEN.PK113-7D and AS2.4940×Ale28 hybridisation cultures. For CBS12357×CEN.PK113-7D representative examples are shown, 22 isolates were tested in total. Single cell isolates of the parental strains were included as a control, as well as genomic DNA of the hybrid strain IMS0408 (*S. cerevisiae*×*S. eubayanus*). L: Generuler 50 bp DNA Ladder. Arrows indicate hybrids, numbers correspond to different single-cell isolates.

Figure 4:
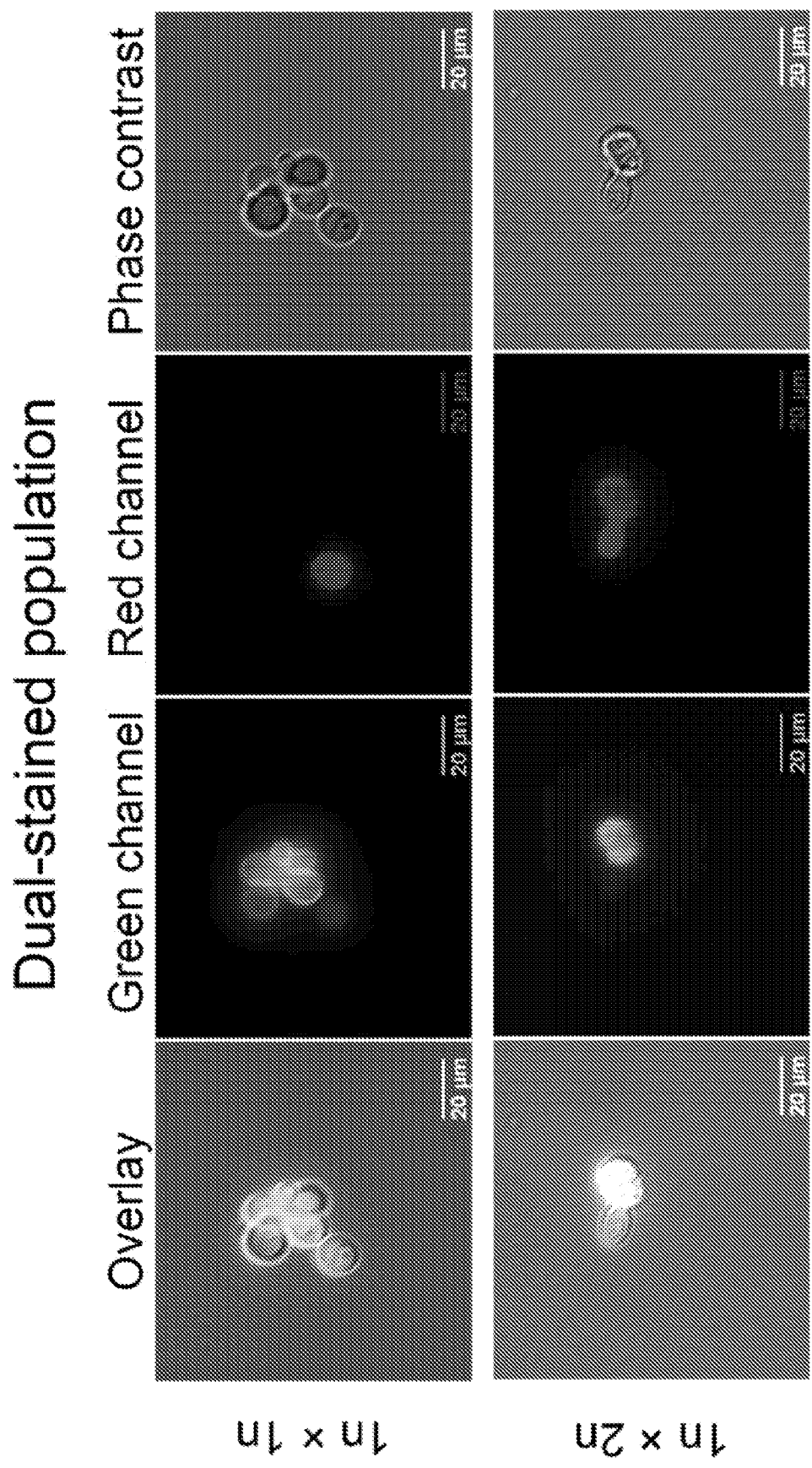
Figure 4:
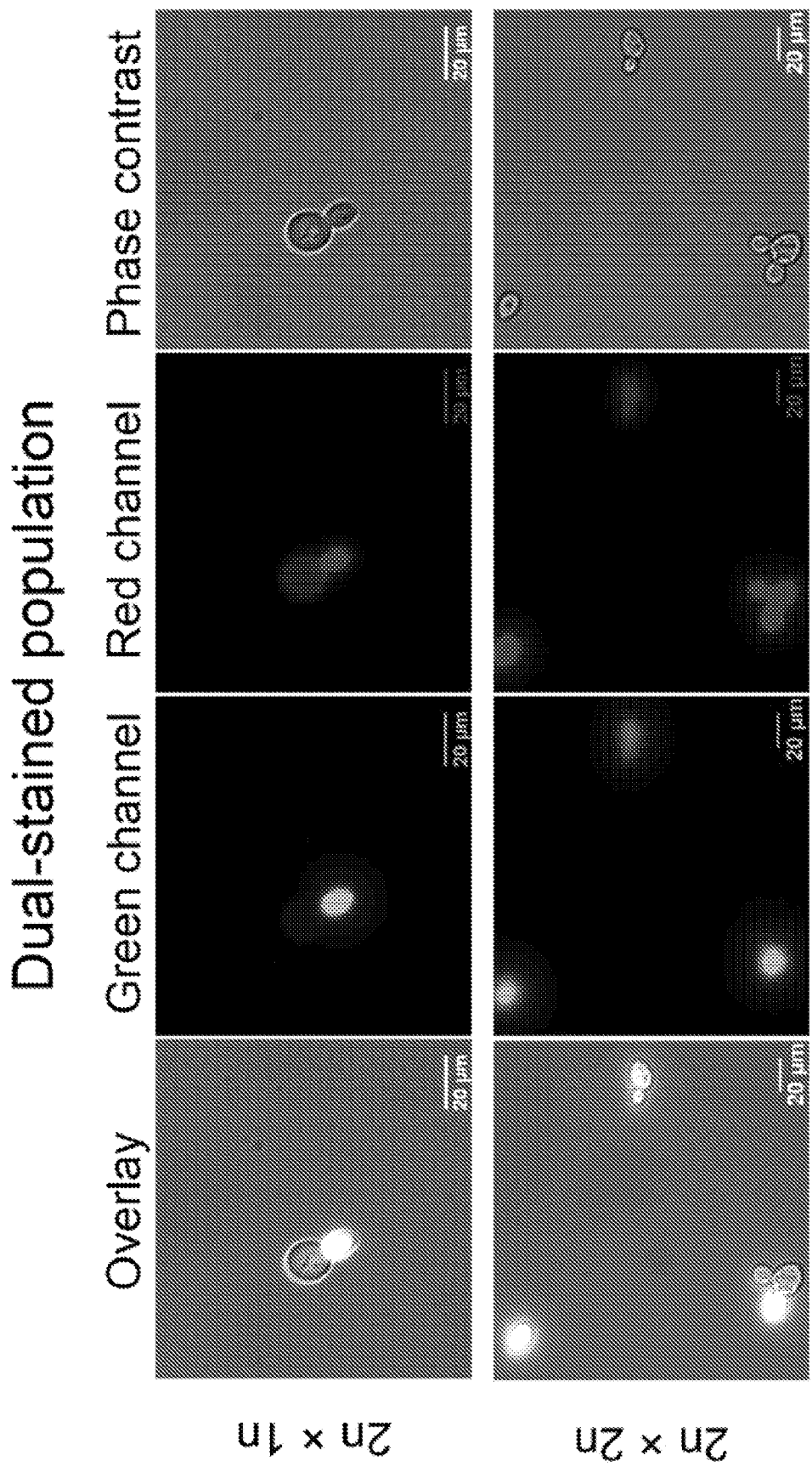

FIG. 4. Fluorescence microscopy images (630×) of hybridization between CFSE-stained *S. eubayanus* and Far Red-stained *S. cerevisiae* cells of different ploidies sorted from the dual-stained population measured by FACS analysis. From top to bottom: CBS12357 (*S. eubayanus*, sporulated)×IMK439 (*S. cerevisiae*, MATa ura3Δ::KanMX), CBS12357 (sporulated)×IMX1471 (*S. cerevisiae*, MATa/a ura3Δ::KanMX/ura3Δ::KanMX), CBS12357 (diploid)×IMK439 and CBS12357 (diploid)×IMX1471.

Figure 5:
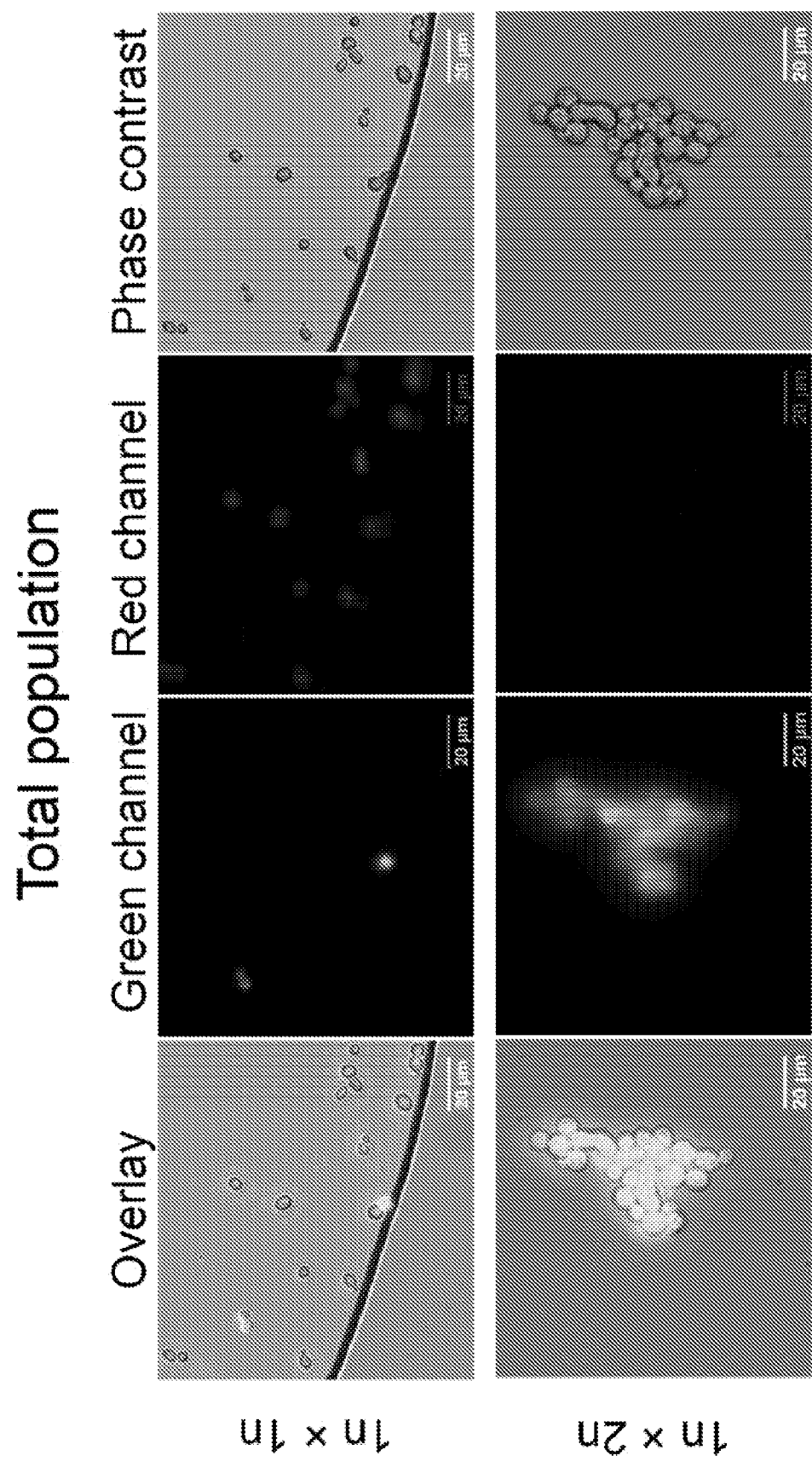
Figure 5:
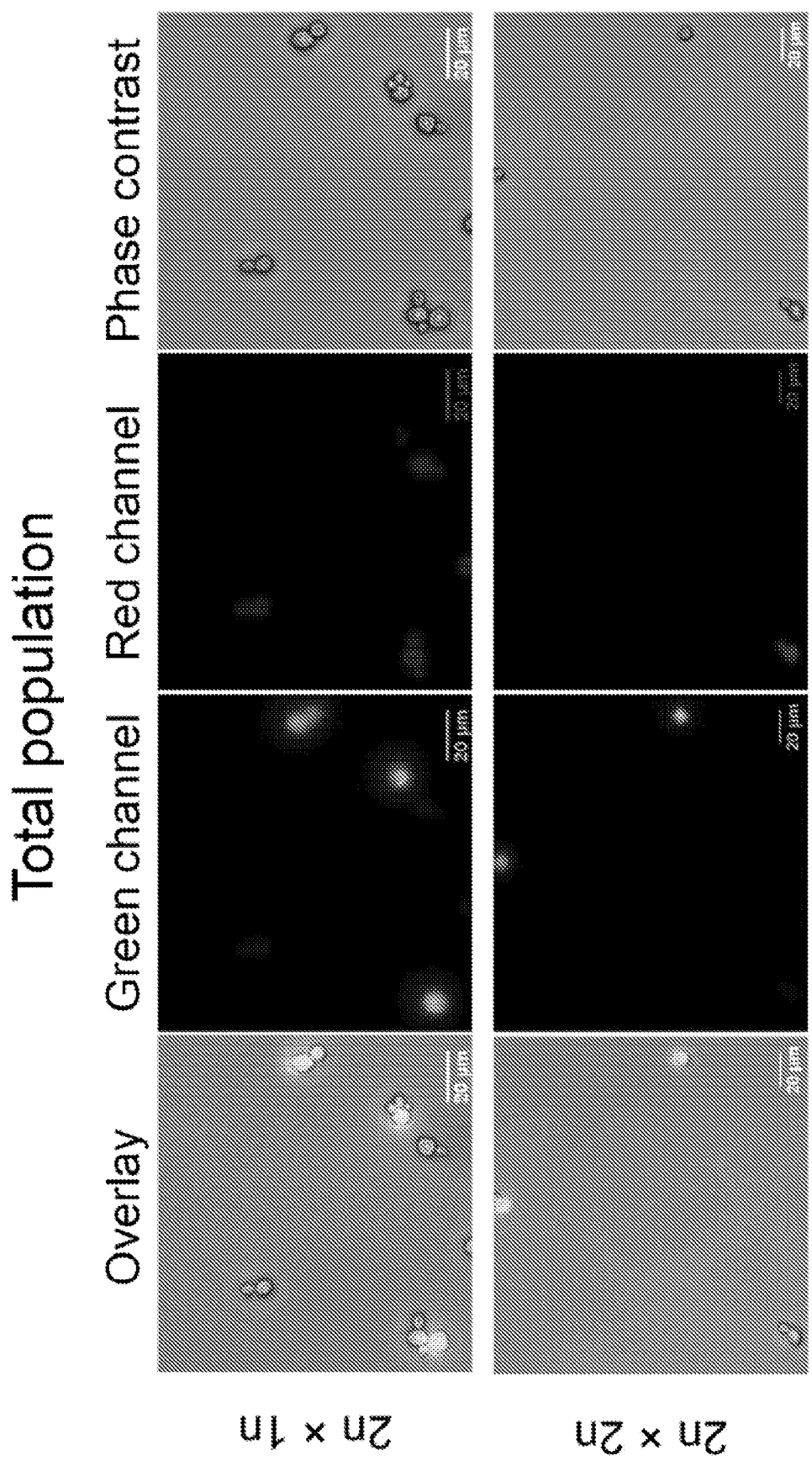

FIG. 5. Fluorescence microscopy images (630×) of hybridization between CFSE-stained *S. eubayanus* and Far Red-stained *S. cerevisiae* cells of different ploidies from an unenriched mating culture. From top to bottom: CBS12357 (*S. eubayanus*, sporulated)×IMK439 (*S. cerevisiae*, MATa ura3Δ::KanMX), CBS12357 (sporulated)×IMX1471 (*S. cerevisiae*, MATa/a ura3Δ::KanMX/ura3Δ::KanMX), CBS12357 (diploid)×IMK439 and CBS12357 (diploid)×IMX1471.

Figure 6:
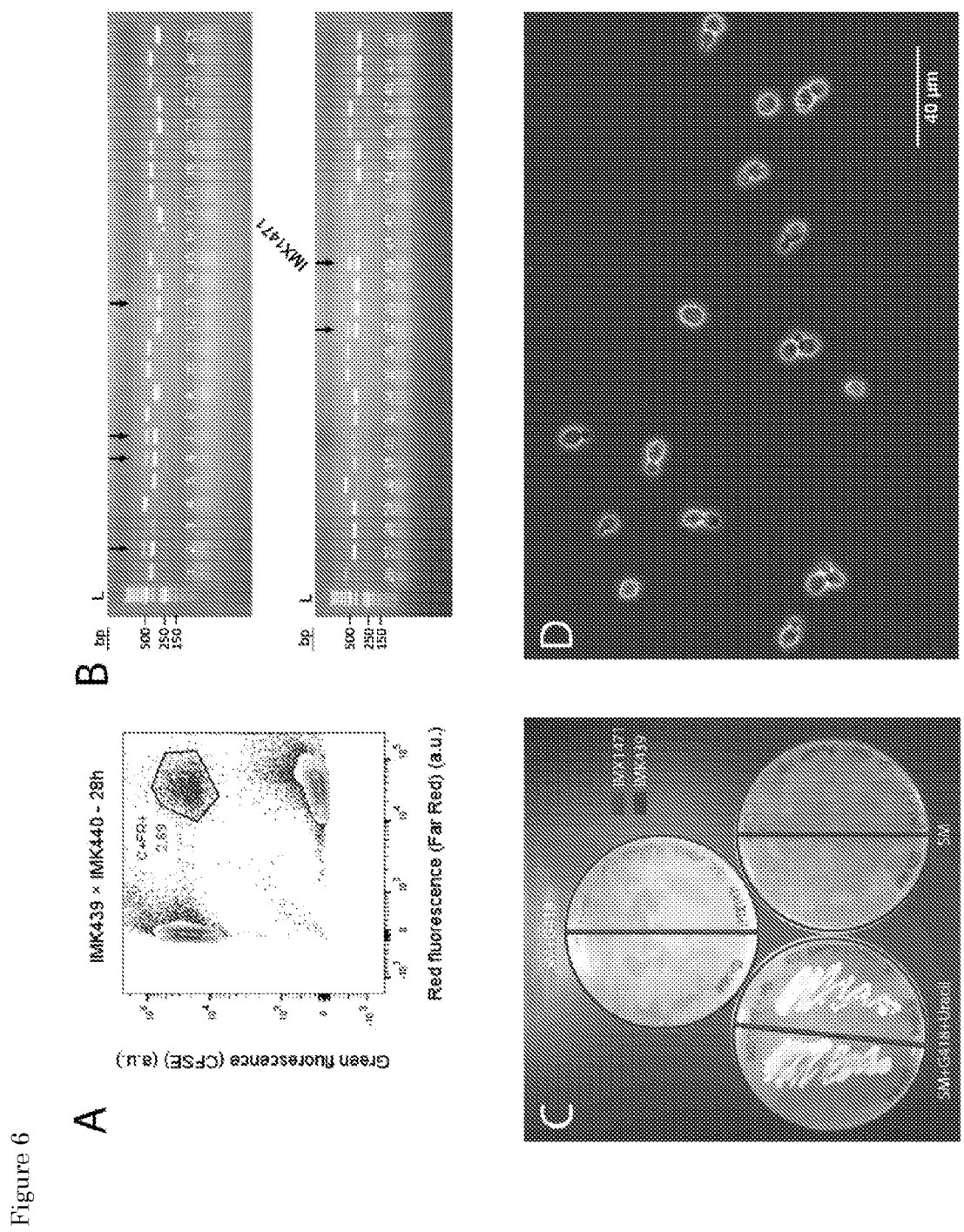
Figure 6:
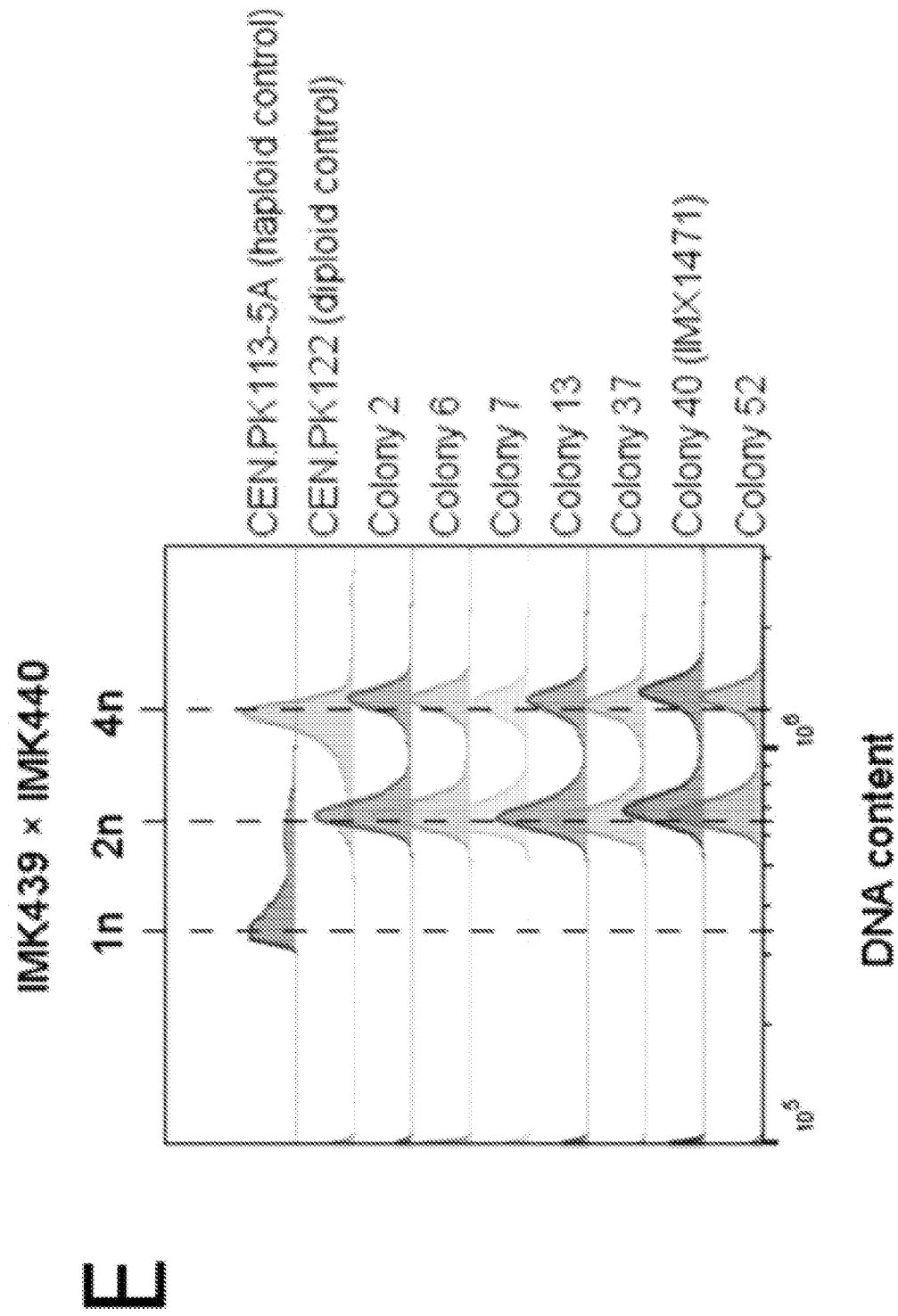

FIG. 6. Construction and validation of IMX1471 by mating IMK439 (*S. cerevisiae*, MATa ura34::KanMX) with IMK440 (*S. cerevisiae*, MATa ura3Δ::KanMX). (A) Contour plots of fluorescence intensities of stained IMK439 (CFSE)

and IMK440 (Far Red) cells after 30 h of mating on YPD. 100'000 cells were analysed, the green and red fluorescence intensity of each cell is shown. The gated areas were used for sorting cells, event rates of each gate are indicated as a percentage. (B) Multiplex colony PCR for confirmation of the presence of MATa and MATα in single-cell isolates of the dual-stained population from a IMK439×IMK440 mating culture. Mating type was determined with primers 11 (SEQ ID NO: 5), 12 (SEQ ID NO: 6) and 13 (SEQ ID NO: 7) (Supplementary table 3). L: Generuler 50 bp DNA Ladder, arrows indicate mated cells, numbers correspond to different single-cell isolates. (C) Verification of presence of genetic markers in IMK439 and IMX1471 by plating on synthetic minimal medium (SM), SM+G418 and SM+G418+Uracil. (D) Microscope image (400×) showing sporulation ability of IMX1471. (E) Ploidy assessment of mated IMK439× IMK440 cells. DNA content of CEN.PK122 (diploid), CEN.PK113-5A (haploid), and mated cells was measured by DNA staining and flow cytometry.

DETAILED DESCRIPTION OF THE INVENTION

Definitions

The term "hybrid" or "hybrid organism", as is used herein, refers to an organism that is the result of combining genomes of two organisms of different varieties, species or genera. A hybrid preferably is the result of sexual crossing, meaning that the hybrid organism is the result of fusion of two cells of different sex, such as two cells of different mating types, preferably two gametes.

The term "interspecies hybrid", as is used herein, refers to an organism that is the result of combining genomes of two organisms of different species or genera.

The terms "first parent organism" and "second parent organism", as are used herein, refer to two organisms of different varieties, species or genera. Said two organisms are hybridization-compatible.

The term "hybridization-compatible", as is used herein, refers to two organisms that can be crossed, preferably sexually crossed. When the two organisms are yeast organism, the term "mating compatable" may be used, which equals the term "hybridization-compatible".

The terms "dye A" and "dye B" refer to different fluorescent dyes that can be used to stain cells.

The term "optimal growth temperature", as is used herein, refers to the temperature at which the cells from a first parent organism and from a second parent organism growth optimally, meaning that cells complete a full cell cycle fastest. Most plants, algae and yeast have an optimal growth temperature between 10 and 50° C., preferably between 15 and 40° C., such as between 18° C. and 25° C., more specifically between 20° C. and 22° C.

The term "auxotrophic marker", as is used herein, refers to marker genes that encode key enzymes in metabolic pathways towards essential metabolites, especially monomers, used in biosynthesis. An example is the URA3 gene, which encodes orotidine-5'-phosphate decarboxylase, an essential enzyme in pyrimidine biosynthesis in *Saccharomyces cerevisiae*. Similarly, HIS3, LEU2, TRP1, and MET15 marker genes encode essential enzymes for de novo synthesis of the amino acids histidine, leucine, tryptophan, and methionine, respectively. The presence of an auxotrophic marker allows growth of cells in the absence of the corresponding essential metabolite.

The term "gamete", as is used herein, refers to a haploid cell that may fuse with another haploid cell during fertilization. Said haploid cell results from a reductive cell division process termed meiosis. Most organisms have two morphologically distinct types of gametes. Some organisms, including yeast, have morphologically identical types of gametes that, however, differ in allele expression in one or more loci termed mating-type regions. Most plants, algae and yeast organisms can cycle between a diploid and a haploid stage.

The term "diploid", as is used herein, refers to a cell or an organism comprising of two sets of chromosomes. One set of chromosomes is obtained from one parent, while a second set of chromosomes normally is obtained from a second parent. The term "diploid" is used to separate cells and organisms having two sets of chromosomes, from cells and organisms having one set of chromosomes, termed haploid, and from cells and organisms having multiple sets of chromosomes, termed polyploid. Polyploid cells and organisms include triploid, tetraploid, pentaploid, hexaploid and octaploid cells and organisms.

The term "aneuploid", as is used herein, refers to a cell or an organism in which not all chromosomes are present in the same number of copies. Hence, the chromosome complement can not be indicated as a defined number of complete chromosome sets, such as n, 2n, 3n, or 4n, as is known to a person skilled in the art. The term aneuploidy refers to the presence of an abnormal number of chromosomes in a cell or organism, in contrast to an euploid cell. An aneuploid cell may miss or have an extra part of a chromosome, or may miss one or more chromosome or have one or more chromosomes extra.

The term "germination", as is used herein, refers to the process by which a seed or a gamete recovers the ability to grow vegetatatively, resulting in multicellular structures or in cell replication by mitotic growth. The most common example of germination is the sprouting of a seedling from a seed. In addition, the growth of a sporeling from a spore, such as the spores of hyphae from fungal spores, is also termed germination. In addition, the process in which a fungal spore sheds its spore wall and recovers normal metabolic activity, such as occurs in yeasts is also termed germination. Germination often depends on conditions such a temperature, humidity, oxygen supply and sometimes light or darkness.

The term "microorganism", as is used herein, refers to a unicellular or multicellular eukaryotic organism such as a fungus including a yeast and a protist such as algae. Most microorganisms are unicellular.

The term "yeast", as is used herein, refers to eukaryotic, unicellular microorganisms that are classified as members of the kingdom fungus. A most preferred yeast is a *Saccharomyces sensu stricto* complex. The *Saccharomyces sensu stricto* complex currently encompasses nine different species: *Saccharomyces cerevisiae, S. paradoxus, S. cariocanus, S. uvarum, S. mikatae, S. kudriauzevii, S. arboricola, S. eubayanus* and the recently discovered *S. jurei* [Hittinger, 2013. Trends Genet 29: 309-317; Naseeb et al., 2017. Int J Syst Evol Microbiol 67: 2046-2052].

Cells

Cells of an organism may be grown in a suitable medium comprising, for example, peptone/yeast extracts, or in synthetic medium. If required, a suitable compound enabling growth in presence of a specific genetic marker, for example G418 (2R,3S,4R,5R,6S)-5-Amino-6-[(1R,2S,3S,4R,6S)-4, 6-diamino-3-[(2R,3R,4R, 5R)-3,5-dihydroxy-5-methyl-4-methylaminooxan-2-yl]oxy-2-hydroxycyclohexyl]oxy-2-(1-hydroxyethyl)oxane-3,4-diol), may be added to grow specifically cells that are resistant to such compound.

Homothallic diploid cells, especially homothallic diploid yeast cells, are preferably sporulated and germinated to obtain haploid gametes, before staining and mating. As an alternative, diploid cells may be stained and mated directly as diploids.

For sporulation, cells may be isolated, for example by filtration and/or centrifugation, washed, for example with phosphate buffered saline or with sterile water and resuspended in sporulation medium, for example in 1% (w/v) potassium acetate, 0.02% (w/v) raffinose, adjusted to pH=7 by addition of KOH, and supplemented with adenine, arginine, histidine, isoleucine, leucine, lysine, methionine, threonine, tryptophan, tyrosine, valine and/or uracil, dependent on the specific organism. Cells are preferably incubated in plates or tubes that allow sufficient aeration, as sporulation has high respiratory requirements.

Sporulation is preferably performed for at least 48 hours, preferably between 48 and 96 hours, preferably about 72 h, at 15-25° C., preferably about 20° C. Cells are preferably shaken at about 200 RPM during sporulation.

Following sporulation, spores may be isolated as is known to a person skilled in the art. Suitable protocols for sporulation and isolation of spores are known, including Beckman and Payne, 1983. Phytopathol 73: 286-289; El-Gholl, et al., 1982. Can J Botany 60: 862-868; Wang et al., 2016. Nature Scientific Reports 6: 24923; Alani et al., 1990. Cell 61: 419-436.

For germination, spores are preferably incubated in a suitable medium, preferably a rich medium such as YPD, for a period of at least 1 hours, for example 2-10 hours, preferably about 5 hours. It is preferred that the spores are stirred during incubation. Incubation preferably is at an optimal growth temperature, for example between 20 and 35° C., preferably at about 30° C.

Staining of Cells

Cells of a first and a second organism are stained with a cell-staining fluorescent dye. Said cell-staining dye preferably is non-toxic and suitable for permanently labelling cells with the fluorescent dye in vivo and/or in vitro. Said cell staining or cell labelling preferably does not affect cell morphology and/or cell physiology.

Said cell labelling may be performed by direct or indirect labelling. Indirect labelling includes use of, for example, secondary antibodies that are labelled with the fluorescent dye and the use of tagged compounds, for example tagged proteins, against which an antibody comprising a fluorescently labelled dye is used.

Labelling preferably is direct. Labelling is preferably preformed by labelling primary amines (R—NH2) of proteins, amine-modified oligonucleotides, and other amine-containing molecules.

For this, a dye preferably comprises a succinimidyl group, preferably a succinimidyl ester, to couple the dye to intracellular lysine residues and other amine sources. Further preferred dyes include thiol-reactive dyes, in which a fluorescent label is coupled to, for example, iodoacetamide, maleimide, benzylic halide or a bromomethylketone. In addition, microinjectable dyes comprising a polar dye such as lucifer yellow CH, Cascade Blue hydrazide, Alexa Fluor hydrazides and biocytin that may be introduced into a cell by whole-cell patch clamping, iontophoresis, osmotic lysis of pinocytic vesicles; and/or fluorescent dextran conjugates or fluorescent microspheres that may be loaded into cells by invasive techniques such as microinjection, whole-cell patch clamping, scrape loading, microprojectile bombardment, electroporation or osmotic shock, can be used to stain cells in methods of the invention.

Said fluorescent label preferably is selected from Abz (Anthranilyl, 2-Aminobenzoyl), N-Me-Abz (N-Methyl-anthranilyl, N-Methyl-2-Aminobenzoyl), FITC (Fluorescein isothiocyanate), 5-FAM (5-carboxyfluorescein), 6-FAM (6-carboxyfluorescein), TAMRA (carboxytetramethyl rhodamine), Mca (7-Methoxycoumarinyl-4-acetyl), AMCA or Amc (Aminomethylcoumarin Acetate), Dansyl (5-(Dimethylamino) naphthalene-1-sulfonyl), EDANS (5-[(2-Aminoethyl)amino]naphthalene-1-sulfonic acid), Atto (e.g. Atto465, Atto488, Atto495, Atto550, Atto647), cyanine (Cy) dyes, including Cy3 (1-(5-carboxypentyl)-3,3-dimethyl-2-((1E,3E)-3-(1,3,3-trimethylindolin-2-ylidene)prop-1-en-1-yl)-3H-indol-1-ium chloride), Cy5 (1-(5-carboxypentyl)-3, 3-dimethyl-2-((1E,3E,5E)-5-(1,3,3-trimethylindolin-2-ylidene)penta-1,3-dienyl)-3H-indolium chloride), including trisulfonated Cy5, and Cy7 (1-(5-carboxypentyl)-2-[7-(1-ethyl-5-sulfo-1,3-dihydro-2H-indol-2-ylidene)hepta-1,3,5-trien-1-yl]-3H-indolium-5-sulfonate), Alexa Fluor (e.g. Alexa Fluor 647, Alexa488, Alexa532, Alexa546, Alexa594, Alexa633, Alexa647), Bodipy (e.g. Bodipy® FL), Dylight (e.g. DyLight 488, DyLight 550), Lucifer Yellow (ethylene diamine or 6-amino-2-(2-amino-ethyl)-1,3-dioxo-2,3-dihydro-1H-benzo[de]isoquinoline-5,8-disulfonic acid) and derivatives thereof.

Cells of a first organism may be labeled with a first dye, herein after termed dye A, while cells of a second organism may be labeled with a second dye, herein after termed dye B. Dye A and dye B are fluorescent dyes, whereby dye A differs from dye B. In addition, cells labelled with dye A preferably can be distinguished from cells labelled with dye B; for example by employing dyes with different excitation and/or emission spectra. Suitable dyes that can be used in methods of the invention can be excited by a monochromatic light source, preferably a laser, more preferably by an ultraviolet laser (about 355 nm). a violet laser (about 405 nm), a blue laser (about 488 nm) or a red laser (about 640 nm). For example, dye A may be a dye that is excited with a red laser at about 630 nm, and which emits at about 661 nm, while dye B is a dye that is excited with a blue laser at about 492 nm and which emits at about 517 nm.

It will be clear to a person skilled in the art that preferred dye combinations include dyes that can be distinctly measured, preferably by two emission filters without spectral overlap, preferably without the need for fluorescence compensation, more preferably dyes that can be excited by two different by two different lasers to minimize spectral overlap, such as with a violet laser (about 405 nm), a blue laser (about 488 nm) or a red laser (about 640 nm). Preferred combinations, which allows cells that are stained with dye A to identify and isolate from cells stained with dye B are fluorescent dyes that can be excited with a violet laser and a blue laser; with a violet laser and a red laser, or with a blue laser and a red laser.

Dye A and dye B preferably are dyes that also allow the identification and isolation of cells that harbor both dye A and dye B, from cells that harbor only dye A and only dye B. For this, preferred dyes include a dye that is excited with a red laser at about 630 nm, and which emits at about 661 nm, and a dye that is excited with a blue laser at about 492 nm and which emits at about 517 nm.

Staining of cells can be performed by methods known in the art. For example, cells of an organism may be incubated with a dye, preferably a succinimidyl ester-coupled dye, for a period of time, preferably between 0.1 hour and 1 day, preferably between 10 minutes and overnight. It is preferred that cells are concentrated, for example by filtration or centrifugation, followed by incubation in a balanced electrolyte solution, Staining preferably is performed at a reduced temperature to prevent cell proliferation. Therefore, staining preferably is performed at a temperature below 20° C., preferably between 5° C. and 15° C., more preferably between 10° C. and 13° C., most preferably about 12° C. By reducing the temperature, cell division takes longer.

Staining, and further mating and processing of stained cells, preferably is performed under reduced light conditions, preferably in the dark.

Hybridization of Cells

The production of a hybrid organism through fusion of cells is called hybridization. If the cells are somatic cells that are hybridized under in vitro conditions, the term somatic hybridization is applicable.

In vitro somatic cell hybridization was first discovered by the group of George Barski (Barski et al., 1960. C R Hebd Seances Acad Sci 251: 1825-7). Spontaneous hybridization is rare. Hybridization of stained parent organisms may be induced either chemically, for example with polyethylene glycol, or with inactivated virus, for example Sendai Virus. Protocols for generating hybrids, including interspecies hybrids, are known. Examples of such protocols are present in, for example, Grosser et al., 1996. Theor Appl Genet 92: 577-582; Kisaka et al., 1998. Plant Cell Rep 17: 362-367; Matsumoto et al., 2002. Euphytica 125: 317-324.

If the parent organism are yeasts, hybridization or mating may be performed by incubating stained parent cells in rich medium, for example 1% (w/w) yeast extract, 2% (w/w) peptone and 2% (w/w) glucose.

For hybridization, stained cells may be brought in close contact with each other, for example by filtration or centrifugation, followed by incubating the cells in an appropriate medium.

Hybridization preferably is performed at a temperature that is below the optimal growth temperature of the parent organism, in order to prevent excessive cell proliferation. By reducing the temperature, cell division takes longer, while hybridization is less affected. Hence, a higher proportion of the resulting cells are hybrid cells, when compared to hybridization at a higher temperature. A hybridization temperature that is at least 5° C. below the optimal growth temperature of the parent organisms was found to limit loss of staining by the dyes and to result in identification of rare interspecies hybrids resulting from hybridization between the first parent organism and the second parent organism.

A temperature that is at least 5° C. below the optimal growth temperature of the first and/or the second parent organism is preferably below 18° C., preferably between 5° C. and 15° C., more preferably between 10° C. and 13° C., most preferably about 12° C. A person skilled in the art is unquestionably able to determine an optimal growth temperature of a plant, an alga and/or a yeast with an unusual optimal growth temperature, for example by growing cells of the plant, alga and/or yeast at different temperatures.

Hybridization of cells is preferably performed in the dark to prevent bleaching of the fluorescent dyes, as will be clear to a person skilled in the art.

Hybridization preferably performed by statically incubating the cells of the first and second parent organisms in the dark at a temperature of at least 5° C. below the optimal growth temperature for a period of at least 2 hours, preferably for a period of between 2 and 48 hours, such as 12 hours, 16 hours, 24 hours and 36 hours. A preferred period is overnight, which routinely is about 16 hours.

Isolation of Cells

Following hybridization of cells of the first and second parent organisms, hybrid cells such as interspecies hybrid cells, are identified and separated from the first and second parent organisms. Because cells from the first parent organism are stained with fluorescent dye A and cells from the second parent organism are stained with dye B; hybrid cells such as interspecies hybrid cells can be isolated on the basis of a staining with both dye A and with dye B. For example, if cells of the first parent are stained with carboxyfluorescein, and cells of the second parent are stained with Far Red, hybrid cells with be visible as emitting at about 661 nm when excited with a red laser at about 630 nm, and emitting at about 517 nm when excited with a blue laser at about 492 nm.

Such dual stained hybrid cells can be isolated from singular stained cells by any method known in the art. For example, a microscope equipped with a micromanipulator may be used to identify and isolate dual labelled hybrid cells.

A preferred method to sort dual labelled cells comprises a flow cytometry technique such as fluorescent activated cell sorting (FACS). A FACS has the additional advantage that the morphology of the cells can simultaneously be analysed by forward scatter and side scatter. Based in the staining pattern and the forward/side scatter, sorting gates can be set to determine the types of cells to be sorted. Gated single cells can be isolated in individual receptacles, for example in well of a multiwell plate such as a 96-well microtiter plate.

Following isolation of single hybrid cells, they may be grown in the individual receptacles. In case the gated cells comprise false positive hybrid cells comprising closely associated cells of the first and second parent that were scored as double stained singular cells, the isolated dual labelled cells may be subjected to a second round of identifying a hybrid organism as a dual labelled cell and isolating the dual labelled cell from singular labelled cells. The dyes that are used for this second round may be identical or different from the dyes that are used in the first round, as long as a hybrid organism can be isolated as a dual labelled cell from singular labelled cells.

Prior to the second round of identifying a hybrid organism, associated cells may be detached by incubating the cells, for example, with a detergent and/or sonicating or vortexing the cells, as is known to a person skilled in the art. In addition, cells may be incubated in the presence of a chelating agent, for example ethylenediaminetetraacetic acid, a surfactant and/or an enzyme such as zymolyase and/or lyticase.

As an alternative, or in addition, the ploidy of the cells may be determined, for example by flow or laser-scanning cytometry. Such method relies on labeling cells with a fluorochrome that is expected to stain DNA stoichiometrically and thus accurately report DNA content. For analytical purposes, a portion of the cells may be permeabilized by a detergent and/or a fixative such as methanol or ethanol and labeled with a DNA-specific fluorochrome. For example, a sample of the cells may be fixed, for example using ethanol, and stained with a nucleic acid stain such as SYTOX® Green Nucleic Acid Stain (Invitrogen S7020). Preferably, a fluorochrome which can penetrate into live cells due to innate permeability of the cellular membrane is used, such as Vybrant™ Dyecycle™ dyes (ThermoFisher Scientific). Fluorescence of the samples may be determined on a flow cytometer, using a laser and emission filter suitable for detection of the DNA-binding fluorescent stain. Suitable conditions may be excitation with a 488 nm laser and detecting emission through a 533 bandpass filter with a bandwidth of 30 nm. Cells may be sorted that have the expected ploidy which is the summed ploidy of the first and second parent organisms. For example, when a first parent organism is haploid (1N), and a second parent organism is diploid (2N), a hybrid organism can be scored as 3N.

For the purpose of clarity and a concise description, features are described herein as part of the same or separate embodiments, however, it will be appreciated that the scope of the invention may include embodiments having combinations of all or some of the features described.

EXAMPLES

Example 1

Materials and Methods
Strains, Media and Cultivation

The *S. cerevisiae* and *S. eubayanus* strains used in this study are listed in Table 1. Strains were routinely grown in complex medium (YP), containing 10 g L-1 yeast extract and 20 g L-1 peptone supplemented with 20 g L-1 glucose for YPD and with 20 g L-1 trehalose for YPT. Synthetic medium (SM) containing 20 g L-1 glucose, 3 g $L^{-1}$ KH2PO4, 5.0 g $L^{-1}$ (NH4)2SO4, 0.5 g $L^{-1}$ MgSO4·7 H2O, 1 mL $L^{-1}$ of a trace element solution and 1 mL $L^{-1}$ of a vitamin solution, was prepared as described previously [Verduyn et al., 1992. Yeast 8: 501-517], and the pH was set to 6.0 using 2 M KOH. Selection for the KanMX marker was performed in SM+G418, which corresponds to SM medium supplemented with 0.2 g $L^{-1}$ of G418 (Invitrogen, Carlsbad, Calif., USA) in which (NH4)2SO4 was replaced by 1 g $L^{-1}$ monosodium glutamate as ammonium sulfate impedes G418 [Cheng et al., 2000. Nucleic Acids Res 28: e108-e108]. For solid media, 20 g L-1 agar was added to media. Sporulation was performed in sporulation medium, containing 2% potassium acetate with the pH set to 7.0 using acetic acid [Bahalul et al., 2010. Yeast 27: 999-1003]. *Saccharomyces* strains were propagated in YPD in either 500 mL round-bottom shake flasks with a working volume of 100 mL or in 50 mL Greiner Polypropylene Filter Top Tubes with a working volume of 30 mL. *S. cerevisiae* and *S. eubayanus* cultures were grown at 30° C. and 20° C., respectively, at 200 RPM in an Innova®44 incubator shaker (Eppendorf, Nijmegen, the Netherlands). Frozen stocks were prepared by addition of glycerol (30% v/v) to exponentially growing shake-flask cultures and stored aseptically in 1 mL aliquots at −80° C.
Staining of *Saccharomyces* Cultures For staining, CellTrace™ Violet, CellTrace™ CFSE and CellTrace™ Far Red fluorescent dyes (Thermo Fisher Scientific, Waltham, Mass., USA) were prepared according to the manufacturers' recommendations. Cultures were stained with 2 µL CellTrace™ dye per mL culture and incubated overnight in the dark at 12° C. and 200 RPM. Dyed cultures were washed twice with YP medium to remove any leftover dye by binding to the yeast extract and peptone.
Intraspecific Mating For intraspecific mating experiments, two heterothallic haploid *S. cerevisiae* strains were propagated until mid-logarithmic phase. The cultures were washed and diluted in sterile Isoton II (Beckman Coulter, Woerden, NL) to a final cell density of approximately 106 cells mL-1 and stained with CellTrace™ Violet and CellTrace™ CFSE as described. The two stained cultures were mated by pipetting them together into one Greiner tube. The cells were pelleted and resuspended in YPT. The mating culture was transferred to an Eppendorf tube and centrifuged briefly (2000 g, 1 min) to increase proximity of the cells for more efficient mating. Subsequently, the mating culture was statically incubated at 12° C. in the dark until FACS analysis.
Interspecies Mating and Rare Mating Homothallic diploid strains were sporulated and germinated prior to staining and mating to obtain haploid gametes which could readily mate with the homothallic haploid gametes or heterothallic haploid cells of the other species. For rare mating, diploid strains were either treated as above or stained and mated directly as diploids. For sporulation, 10 mL of stationary phase culture was spun down, washed with sterile demineralized water and resuspended in 9 mL of sporulation medium in a 50 mL Polypropylene Filter Top Tubes to ensure sufficient aeration, as sporulation has high respiratory requirements [Sherman, 1963. Genetics 48: 375]. Sporulation cultures were incubated for at least 72 h at 20° C. and 200 RPM. The presence of asci was determined using microscopy. By default, spores were isolated as described by Herman and Rine [Herman and Rine, 1997. EMBO J 16: 6171-6181] with minor modifications. In short, spores were pelleted (1000 g, 5 min), resuspended in in softening buffer (10 mM dithiothreitol, 100 mM Tris-SO4, pH set to 9.4 with H2SO4) and incubated at 30° C. for 10 minutes. Cells were washed using demineralized water, resuspended in spheroplasting buffer (2.1 M sorbitol, 10 mM KH2PO4, pH set to 7.2 with 1M NaOH) with 0.8 gL-1 Zymolyase 20-T (AMS Biotechnology Ltd., Abingdon, UK) and incubated overnight at 30° C. After incubation, the culture was pelleted (1000 g, 10 min), washed using demineralized water and resuspended in 0.5% Triton X-100. The spores were sonicated for approximately 15 s at 50 Hz with an amplitude of 6 micron while kept on ice. During initial optimization of the protocol, a short protocol where only the Zymolyase-step was used was also tested. The isolation of spores was confirmed using a microscope and isolated ascospores were either stored at 4° C. or immediately used. For germination, spores were by default washed once with YPD and subsequently resuspended in 20 mL YPD to a concentration of approximately $10^6$ cells mL-1. The germination culture was incubated in a 100 mL round bottom flask at 30° C. and 200 RPM for 5 h. A protocol using 2% glucose instead of YPD as well as germination on YPD for different times was tested during initial optimization of the interspecies hybridization. By default, the haploid *S. eubayanus* and *S. cerevisiae* strains were washed and diluted in sterile Isoton II (Beckman Coulter) to a final cell density of approximately $10^6$ cells mL-1 and stained with CellTrace™ Violet and CellTrace™ CFSE as described. For rare mating, a final cell density of approximately 20×$10^6$ cells mL-1 was used and cells were stained with CellTrace™ Far Red and CellTrace™ CFSE as described. Two stained cultures were mated by pipetting them together into one Greiner tube. The cells were pelleted and resuspended in YPD. The mating culture was transferred to an Eppendorf tube and centrifuged briefly (2000 g, 1 min) to increase proximity of the cells for more efficient mating. The mating culture was statically incubated at 12° C. in the dark until FACS analysis.
FACS Analysis and Sorting Cultures for FACS analysis and sorting were diluted in sterile Isoton II and vortexed briefly to disrupt cell aggregates. For rare mating, 50 mM EDTA was added to disrupt any nonsexual flocculation. The cultures were analysed on a BD FACSAria™ II SORP Cell Sorter (BD Biosciences, Franklin Lakes, N.J., USA) equipped with 355 nm, 445 nm, 488 nm, 561 nm and 640 nm lasers and a 70 µm nozzle, and operated with filtered FACSFlow™ (BD Biosciences). Correct cytometer performance was evaluated prior to each experiment by running a CST cycle with corresponding CS&T Beads (BD Biosciences). Drop delay for sorting was determined by running an Auto Drop Delay cycle with Accudrop Beads (BD Biosciences). CellTrace™ Violet fluorescence was excited by the 355 nm laser and emission was detected through a 450 nm bandpass filter with a bandwidth of 50 nm, CellTrace™ CFSE was excited by the 488 nm laser and emission was detected through a 545 nm bandpass filter with a bandwidth of 30 nm and CellTrace™ Far Red was excited by the 640 nm laser and emission was detected through a 780 nm bandpass filter with a bandwidth of 60 nm. Fluorescence of mating cultures was analysed on either a CFSE versus Violet or a CFSE versus Far Red plot.

Morphology of the cells was analysed by plotting forward scatter (FSC) against side scatter (SSC). For each measurement, at least 100'000 events were analysed. Sorting regions ('gates') were set on these plots to determine the types of cells to be sorted. Gated single cells were sorted in 96-well microtiter plates containing YPD using a "single cell" sorting mask corresponding to a yield mask of 0, a purity mask of 32 and a phase mask of 16. When required, colonies were replica-plated upon growth to 96-well plates with selective medium (SM or SM+G418), using an ethanol-flame sterilized 96-pin replicator. FACS data was analysed using FlowJo® software (version 3.05230, FlowJo, LLC, Ashland, Oreg., USA).

Viability Determination

In order to determine the rate of viability or mating efficiency in cultures with low viability or mating efficiency, Poisson statistics were used. According to Poisson statistics, the chance of a viable colony appearing from a set number of sorted cells in each well can be determined mathematically (Equation 1), where P is an estimate of the chance of a colony appearing and λ is the fraction of living cells per well [Dube et al., 2008. PloS One 3: e287650].

$$\lambda = -\ln(1-P) \qquad \text{Equation 1}$$

The total percentage of hybrid cells is then defined as A multiplied by the amount of wells (W), which yields the corrected amount of true positives. This is divided by the amount of cells sorted to determine the yield of hybrids on the total population (Equation 2).

$$\% \text{ hybrids} = (\lambda * W)/(\text{Total cells sorted}) \qquad \text{Equation 2}$$

For experiments with high viabilities, only 1 cell was sorted in each well so no Poisson correction for the probability of multiple events in one well was applied (Equation 1). Here, the percentage of viability was calculated by counting the amount of colonies and dividing those by the amount of sorted cells.

Imaging

Cells were imaged using a Zeiss Axio Imager Z1 (Carl Zeiss AG, Oberkochen, Germany). For fluorescent imaging, cells were excited with a xenon lamp using different filter sets for different fluorophores. Filter sets were chosen in such a way that bleed-through from one fluorophore into the other channel was minimized. Fluorescence from CellTrace™ CFSE was imaged through a GFP filter set (Carl Zeiss AG) containing a 470 nm bandpass excitation filter with a bandwidth of 20 nm and a 540 nm emission filter with a bandwidth of 25 nm. CellTrace™ Far Red was imaged through a Cy5 filter set (Carl Zeiss AG) containing a 640 nm bandpass excitation filter with a bandwidth of 30 nm and a 690 nm emission filter with a bandwidth of 50 nm. Images were processed using AxioVision SE64 (Rel. 4.9.1. Carl Zeiss AG, Oberkochen, Germany) and FIJI [Schindelin et al., 2012. Nature Methods 9: 676-682].

Ploidy Determination by Flow Cytometry

For ploidy determination, samples were fixed using ethanol as previously described [Hebly et al., 2015. FEMS Yeast Res 15: fov005]. Staining of cells with SYTOX® Green Nucleic Acid Stain (Invitrogen 57020) was performed as described [Haase and Reed, 2002. Cell Cycle 1: 117-121] with some minor modifications. The cells were washed in 50 mM Tris-Cl (pH 7.5) and resuspended in 100 µL RNase solution (1 mg/mL RNase A in 50 mM Tris-Cl). By default, 100 µL of cells was added to 1 mL of SYTOX® Green solution. When processing large amounts of samples, a high-throughput protocol in 96-well microtiter plates was used with a PIPETMAN® M multichannel electronic pipette (Gilson, Middleton, Wis., USA). In this modified protocol, 100 µL sample was fixated by adding 150 µL 70% ethanol and in the final step 20 µL sample was added to 180 µL SYTOX® Green solution. An unstained control was included for every sample. Fluorescence of the samples was measured on a BD Accuri™ C6 CSampler Flow Cytometer (BD Biosciences). The fluorophore was excited with the 488 nm laser of the flow cytometer and emission was detected through a 533 bandpass filter with a bandwidth of 30 nm. Ploidy data was analysed using FlowJo® software (version 3.05230, FlowJo).

Identification of Interspecies Hybrids by PCR

The presence of genetic material from S. cerevisiae and from S. eubayanus was confirmed by PCR. A master mix was prepared, containing water, primers and 2× DreamTaq PCR Mastermix (Life Technologies, Carlsbad, Calif., USA). Primers specific for S. cerevisiae (8570 & 8571, see Table 3) and S. eubayanus (8572 & 8573, Table 3) [Muir et al., 2011. FEMS Yeast Res 11: 552-563; Pengelly and Wheals, 2013. FEMS Yeast Res 13: 156-16153] were added to a final concentration of 0.25 mM of each primer. DNA was isolated by boiling 2 µL of a liquid culture in 2 µL of NaOH for 15 min at 99° C. 18 µL of PCR master mix was added to the template DNA. Cycling parameters for PCR with DreamTaq were: initial denaturation at 95° C. for 2 min, then 35 PCR cycles of 95° C. for 30 s, 55° C. for 30 s and 72° C. for 1 min, ending with a final extension at 72° C. for 10 min. Mating type was determined using the same protocol, but using primers specific for mating type (Table 3). PCR reactions were prepared using a Tecan Freedom EVO® liquid handler (Tecan, Männedorf, Switzerland) or with a PIPETMAN® M multichannel electronic pipette (Gilson). PCR products were separated on a 2% (w/v) agarose gel stained with SERVA DNA Stain G (Serva electrophoresis GmbH, Heidelberg, Germany) in 0.5×TBE buffer (45 mM Tris-borate, 1 mM EDTA, pH 8) for approximately 30 min on 100 V. The gel was imaged using an InGenius LHR Gel Imaging System (Syngene, Bangalore, India).

Results

Isolating intraspecific hybrids from a mating culture using FACS As intraspecific mating occurs more efficiently than interspecies mating, a functional protocol for staining, mating and sorting was developed by mating two heterothallic S. cerevisiae haploid strains. Two strains with complimentary auxotrophies were mated, resulting in prototrophic mated diploids which could grow on synthetic minimal medium (SM), allowing for easy and accurate measurement of the fraction of mated cells in a sample. Strains CEN.PK113-5A (MATa, His-, Lys-, Trp-) and IMK439 (MATα, Ura-) were stained with CFSE and Violet dyes, respectively, and subsequently crossed. The concentration of dye per cell is diluted during each division, resulting in a decrease of intensity of the fluorescent signal per cell over time. To minimize this loss of fluorescence, the mating culture was incubated in YPT at 12° C., as *S. cerevisiae* grows slowly under these conditions. Fluorescence emitted by the cells was measured on a FACS at different time points: before staining, after staining but before mating and after 18 h, 24 h and 42 h of mating (FIG. 1A). A gating area was set around events that showed dual staining, corresponding to putative mated cells, and events within this gating area were sorted on 96-well plates containing YPD to prevent any selective pressure of the present auxotrophic markers. FACS analysis showed that after 18 h a fraction of 0.90% of the mating culture was dual-stained. This number increased to 2.65% after 24 h and to 5.25% after 42 h of mating (FIG. 1A). Under the microscope, "shmoo" morphologies were observed in the dual-stained population (FIG. 1C), which are characteristic of *Saccharomyces* zygotes [Herskowitz, 1988. Microbiol Reviews 52: 536], and confirm the presence of mating cells in this population. Single-cell sorted colonies of dual-stained cells, of single-stained cells and of the total culture were tested for their ability to grow in synthetic minimal medium. Of the dual-stained population, 74-82% was able to grow in selective medium, indicating successful mating (FIG. 1B). Only 4% of the cells from the total mating culture grew in selective medium, indicating a 20-fold enrichment of mated cells in the dual-stained population. Ploidy determination of ten colonies from the dual-stained population by flow cytometry identified three types of ploidy: haploid cells, diploid cells and mixes of both (FIG. 1D). In accordance with previous observations [Bell, 1998. Appl Environment Microbiol 64: 1669-1672], these results indicated that dual-stained events did not consist solely of mated cells, but also of aggregates of stained cells. As mating cells often form aggregates or divide while mating [Lipke and Kurjan, 1992. Microbiol Reviews 56: 180-194], single cell isolation of dual-stained events is necessary to obtain mated cells only. Despite the observed aggregation, the proportion of cells able to grow on selective medium improved to around 20-fold in the dual-stained population and mated cells could easily be obtained after 18 h of mating by plating on SM and verification of ploidy.

Isolation of interspecies hybrids from a mating culture using FACS To investigate whether the developed staining and sorting protocol could also be applied to isolate interspecies hybrids from mating cultures, the diploid wildtype *S. eubayanus* strain CBS12357 was crossed with the haploid *S. cerevisiae* strain IMK439 (MATα, ura3Δ::KanMX). Hybrid cells of these strains would be easily identifiable due to uracil prototrophy and resistance to G418.

As *S. eubayanus* CBS12357 is a homothallic diploid, sporulation and isolation of the spores prior to staining and mating was necessary. As spores from homothallic diploids are able to homodiploidize, efficient separation of the spores in asci is required to minimize self-mating, which would compete with interspecies mating. Therefore, two protocols for digestion of the ascus cell wall were tested: (i) using zymolyase and (ii) using the surfactant Triton X-100 in addition to the zymolyase digestion [Herman and Rine, 1997. EMBO J 16: 6171-6181], the latter resulting in improved separation of the spores (Data not shown). Furthermore, FACS analysis indicated approximately half of the *S. eubayanus* cells was not fluorescent after staining was completed (Data not shown). During germination, the cell wall of a spore is lost. Given the impermeability of the spore cell wall, it is likely to contain much of the fluorescent dye after staining of the spore. Its loss during germination could explain the observed loss of fluorescence. Therefore, an optimal germination method to be used prior to staining was developed by testing germination in 2% glucose and YPD with different incubation durations. After 5 h of germination in YPD the first significant growth was observed, indicating enough time for germination had passed while intraspecific mating was still minimal (Data not shown). Lastly, the ability of *S. eubayanus* to grow or mate with trehalose as a sole carbon source is unknown. Therefore, mating of germinated cells of *S. eubayanus* CBS12357 stained with CFSE and haploid cells of *S. cerevisiae* strain IMK439 stained with Violet dye in YPD medium was compared to mating these strains in YPT medium. The amount of hybrids was assessed over time by sorting the dual-stained population using FACS (FIG. 2A) and replica-plating to selective medium. After 7 h, 1% of the dual-stained population of both mating cultures on YPT and YPD was found to be hybrid. The amount of hybrids in the dual-stained population incubated on YPD increased to 18% after 24 h of hybridization and remained constant after 30 h, while mating on YPT yielded no increase in the number of hybrids (FIG. 2B). After replica-plating a full 96-well microtiter plate of ungated sorted cells to selective medium, no growth was observed, indicating there were less than 0.3% hybrids in the mating culture. This means the culture was enriched at least 70 times for interspecies hybrids by using the optimized protocol for FACS sorting of dual-stained cells (FIG. 2C). This implies that the method of staining and sorting cells using FACS could be applied to enrich for interspecies hybrids and mating on YPD medium for 24-30 h yielded a dual-stained population of which one out of five were true hybrids.

Generation of Marker-Free Interspecies Hybrids

In the previous experiments, the presence of hybrids in the dual-stained population sorted by FACS was verified by growth on selective medium. However, parental strains with complementary selectable phenotypes are not always available or applicable. Therefore, screening methods which do not dependent on the presence of selectable phenotypes in the parental strains are preferable. Hybrids without a selectable phenotype can be identified by amplification of species-specific genes of the parental strains by PCR [Muir et al., 2011. FEMS Yeast Res 11: 552-563; Pengelly and Wheals, 2013. FEMS Yeast Res 13: 156-161] and assessment of the ploidy of cells. However, such screening methods have limited throughput and are only effective on samples with a high frequency of hybrids, such that the amount of cells that has to be screened in order to identify one or more hybrids remains reasonable. When mating IMK439 and spores of CBS12357, 20% of the obtained cells had a phenotype corresponding to the hybrid phenotype, so about 5 cells would have to be screened in order to find a hybrid. To test the possibility of screening for putative hybrids based on a multiplex PCR using primer pairs specific for *S. eubayanus* and *S. cerevisiae*, marker-free *S. eubayanus* and *S. cerevisiae* were crossed. A previously developed PCR-method was used yielding a fragment of 150 bp in the presence of genomic DNA of *S. cerevisiae* with primers 8570 and 8571, and a fragment of 228 bp in the presence of genomic DNA of *S. eubayanus* with primers 8572 and 8573 (Table 3). Because this PCR cannot distinguish a hybrid from a mixed population of two species, a second single-cell sorting step was implemented after propagation of the initially sorted dual-stained cells to ensure single colony isolates were tested. Additionally, the ploidy of the sorted cells was determined with DNA staining and flow cytometry, since uniform ploidy indicated there were no mixed populations as were observed without second sorting (FIG. 1D). To ensure high screening throughput, the multiplex PCR protocol and the ploidy determination protocol were designed such that screening could be automated and executed in 96-well microtiter plates.

To test the proposed method of generating and screening for marker-free interspecies hybrids, two crosses were made. The previous experiment of generating interspecies hybrids with sporulated CBS12357 was repeated, but replacing the genetically modified IMK439 with the marker-free laboratory strain CEN.PK113-7D (MATa) as *S. cerevisiae* parental strain. In parallel, a cross between two industrially-relevant strains was done to investigate whether the presented method could also be applied to generate new potentially industrially relevant hybrids. Industrial strains often have more complex, aneuploid genomes and sporulate poorly, resulting in lower hybridization rates than observed for interspecies hybrids using laboratory strains [Steensels et al., 2014. FEMS Microbiol Reviews 38: 947-995]. *S. eubayanus* strain AS2.4940 (kindly donated by J. Bing [Bing et al., 2014. Current Biol 24: R380-R381), was crossed with Ale28, an industrial ale-type strain of *S. cerevisiae*. Both strains were diploids, so they were sporulated and germinated using the previously discussed optimized protocol to obtain haploid gametes (FIG. 2C). CBS12357 (*S. eubayanus*, sporulated, CFSE) was mated with CEN.PK113-7D (*S. cerevisiae*, MATa, Violet), AS2.4940 (*S. eubayanus*, sporulated, CFSE) was mated with Ale28 (*S. cerevisiae*, sporulated, Violet), and dual-stained populations were sorted from both mating cultures (FIG. 3A). The sorted cells were propagated and a single cell of each colony was sorted again to obtain single-cell isolates. For the CBS12357× CEN.PK113-7D cross, 22 single-cell isolates were obtained and assessment of the species of these isolates showed that 2 isolates were true hybrids (IMH001 & IMH002, FIG. 3B). For the AS2.4940×Ale28 cross, 34 single-cell isolates were obtained of which 5 were identified as hybrids (IMH003-IMH007, FIG. 3B). Therefore, 9% of cells from the mating between CBS12357 and CEN.PK113-7D and 15% of cells from the mating between AS2.4940 and Ale28 were hybrids. DNA content determination by flow cytometry indicated these hybrids were diploid, except for IMH007 which was aneuploid (FIG. 3C). The frequency of hybrids in the dual-stained population was in the same range as the frequency determined using strains harbouring genetic markers and the hybrids were successfully identified by screening using PCR, demonstrating the possibility to identify marker-free hybrids obtained by interspecies mating using the in this study described protocol.

Generation of Interspecies Hybrids by Rare Mating

Many of the hybrids used in industrial processes are polyploid or aneuploid, and this ploidy may contribute to the industrially relevant phenotypes these strains exhibit. Such strains can be constructed by mating strains with higher ploidy. However, only strains of opposite mating type can mate with each other and since diploid strains have mating type a/a, mating can only occur when a spontaneous mating-type switch occurs, yielding a homozygous a/a or α/α mating type. The frequency of this type of mating was reported to be between $10^{-6}$ and $10^{-8}$ [Gunge and Nakatomi, 1972. Genetics 70: 41-58], hence it is called rare mating. As it has been shown that the technique discussed in this study successfully enriches a culture for mated cells, it was investigated whether the enrichment is significant enough to isolate these extremely rare mating events by making different crosses between haploid and diploid *S. eubayanus* and *S. cerevisiae* strains.

In order to allow for easy measurement of rare mating frequencies, strain IMK439 was used as the haploid *S. cerevisiae* parental strain (MATα ura3Δ::KanMX). To obtain strains with a diploid *S. cerevisiae* chromosome complement using the same selectable phenotype, the diploid strain IMX1471 was constructed by intraspecific mating as described previously between IMK439 (*S. cerevisiae*, MATa) stained with CFSE and IMK440 (*S. cerevisiae*, MATa) stained with a new dye, Far Red. Dual-stained cells were sorted and after overnight incubation, single cells from each well were sorted again. A PCR was performed to determine the mating type of the sorted cells using primers 11 (SEQ ID NO: 5), 12 (SEQ ID NO: 6), and 13 (SEQ ID NO: 7) (Table 3), and ploidy, the ability to sporulate and the presence of the uracil auxotrophy and the KanMX marker were tested (FIG. 6). One of the isolates which was MATa/MATα, had a diploid genome content, displayed normal sporulation efficiency and the correct selectable phenotype was stocked as IMX1471 (MATa/α, ura3Δ::KanMX/ura3Δ::KanMX) and used as the diploid *S. cerevisiae* parental strain. CBS12357 was used as *S. eubayanus* parental strain, either as a diploid or after sporulation and germination as a haploid.

In the previous experiments, the separation of the CFSE-stained population and the Violet-stained population was suboptimal; the Violet fluorescence intensity was relatively low and overlapped slightly with the fluorescence emitted by CFSE. As rare mating events have a low frequency, a clear separation of the single-stained and dual-stained population is essential. When constructing strain IMX1471 by mating CFSE- and Far Red-stained parental strains, it was found that the Far Red dye had a stronger fluorescent signal than the Violet dye, leading to clearer separation of the different populations (FIG. 6). Therefore, the Violet dye was replaced by Far Red, which emits light in the red part of the spectrum. The *S. eubayanus* parental strains were stained with CFSE, the *S. cerevisiae* parental strains with Far Red. Four different crosses were made: CBS12357 (sporulated, 1n)×IMK439 (1n), CBS12357 (sporulated, 1n)×IMX1471 (2n), CBS12357 (2n)×IMK439 (1n) and CBS12357 (2n)× IMX1471 (2n). EDTA was added prior to mating to prevent any nonsexual aggregation of CFSE- and Far Red-stained cells [Johnson et al., 1988. Canad J Microbiol 34: 1105-1107]. The frequency of hybrid cells in each mating culture was assessed by plating a fixed amount of mating culture on SM+G418 plates and counting colonies. In parallel, the mating culture was analysed by FACS and the dual-stained population was sorted and replica-plated to SM+G418 to determine the frequency of hybrid cells after sorting. To be able to quantify low frequencies of hybrid cells, wells were inoculated with 1, 10 or 100 dual-stained cells and frequencies were calculated using Poisson statistics. In the unsorted haploid×haploid interspecies mating culture, around one in $4 \times 10^5$ cells grew in selective medium after 24 h, which increased to one in $3 \times 10^4$ after 168 h. In the sorted dual-stained cells from this culture, the occurrence rate increased to an average of one in $3 \times 10^2$, which remained relatively constant over time, corresponding to an average enrichment factor of 700 (Table 2). In the unsorted mating culture between the diploid *S. eubayanus* and the haploid *S. cerevisiae*, none of the plated cells grew in selective medium after 24 h, however the frequencies of hybrid cells increased up to one in $4.7 \times 10^6$ after 168 h. In the sorted dual-stained cells from this culture, the occurrence rate increased to an average of one in $2.4 \times 10^{-3}$, corresponding to an average enrichment factor of 600. In the unsorted mating culture between the haploid *S. eubayanus* and the diploid *S. cerevisiae*, around one in $10^{-7}$ grew in selective medium. After 96 h, sorting of dual stained cells with FACS increased the ratio of hybrid cells by a factor of about 550, resulting in a frequency of hybrid cells of $4.3 \times 10^{-4}$. For the diploid× diploid cross only one hybrid could be obtained from the pool of $20 \times 10^7$ cells by plating all cells, while none were obtained with FACS sorting of 25,664 cells. Overall, while rare mating was possible between the haploid and diploid strains, mated cells were present in very low frequencies both in the mating cultures and in the dual-stained cells. Since the frequencies of hybrid cells obtained by sorting dual stained cells were much lower than with normal mating, around 400 cells need to be sorted for the diploid CBS12357×haploid IMK439 cross, and even more for the other crosses. The Far Red dye and the CFSE dye can be imaged under the microscope without any spectral overlap, therefore unsorted and dual-stained cells of each mating combination were sorted on a glass slide and inspected using fluorescence microscopy. Dual-fluorescent cells were observed in all four mating cultures, also in the cultures where little or no rare mating events were isolated (FIG. 4). Fluorescence of both CFSE and Far Red was usually loca-lised to a part of a budding cell or clusters of cells, although also some homogeneously dual-fluorescent cells were observed, as well as homogeneously single-stained cells. As yeast budding and mating does not occur symmetrically, it is unknown how the stains are transmitted to a daughter cell, therefore it is not sure whether this dual fluorescence is caused by crossover of stains upon mating or has another cause. These dual-stained events were rarely observed in the unenriched mating culture (FIG. 5), which generally contained single-stained cells. This indicates that FACS-sorting of the dual-stained population indeed enriches for dual-stained cells, although not all of them may be viable hybrids.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "VOB-63511-Sequences_ST25.txt", created Nov. 3, 2020, file size of 4,096 bytes, is hereby incorporated by reference.

TABLE 1

Saccharomyces strains used

| Name | Species | Parental strain(s) | Relevant genotype | Origin |
|---|---|---|---|---|
| CEN.PK113-5A | *S. cerevisiae* | — | MATa URA3 his3-Δ1 leu2-3,112 trp1-289 | [Entian and Kötter, 2007. Methods Microbiol 36: 629-666] |
| IMK439 | *S. cerevisiae* | CEN.PK113-7D | MATα HIS3 LEU2 TRP1 ura3Δ::KanMX | [González-Ramos et al., 2013. Biotechnol Biofuels 6: 48] |
| IMK440 | *S. cerevisiae* | CEN.PK113-7D | MATa HIS3 LEU2 TRP1 ura3Δ::KanMX | [González-Ramos et al., 2013. Biotechnol Biofuels 6: 48] |
| CEN.PK122 | *S. cerevisiae* | — | MATa/MATα URA3/URA3 | [Entian and Kötter, 2007. Methods Microbiol 36: 629-666] |
| CBS12357 | *S. eubayanus* | — | MATa/MATα | [Libkind et al., 2011. PNAS 108: 14539-14544] |
| CEN.PK113-7D | *S. cerevisiae* | — | MATa | [Entian and Kötter, 2007. Methods Microbiol 36: 629-666] |
| IMS0408 | *S. eubayanus* × *S. cerevisiae* | CBS12357 × IMK439 | MATa/MATα SeubURA3/Scura3Δ:KanMX | [Hebly et al., 2015. FEMS Yeast Res 15: fov005] |
| AS2.4940 | *S. eubayanus* | — | MATa/MATα | Kindly provided by J. Bing, Chinese Academy of Science [Bing, et al., 2014. Current Biol 24: R380-R381] |
| Ale28 | *S. cerevisiae* | — | MATa/MATα | Kindly donated by HEINEKEN Supply Chain, Zoeterwoude, The Netherlands |
| IMX1471 | *S. cerevisiae* | IMK439 × IMK440 | MATa/MATα ura3Δ::KanMX/ura3Δ::KanMX | This study |
| IMH001 | *S. eubayanus* × *S. cerevisiae* | CBS12357 × CEN.PK113-7D | MATa/MATα | This study |
| IMH002 | *S. eubayanus* × *S. cerevisiae* | CBS12357 × CEN.PK113-7D | MATa/MATα | This study |
| IMH003 | *S. eubayanus* × *S. cerevisiae* | AS2.4940 × Ale28 | MATa/MATα | This study |
| IMH004 | *S. eubayanus* × *S. cerevisiae* | AS2.4940 × Ale28 | MATa/MATα | This study |
| IMH005 | *S. eubayanus* × *S. cerevisiae* | AS2.4940 × Ale28 | MATa/MATα | This study |
| IMH006 | *S. eubayanus* × *S. cerevisiae* | AS2.4940 × Ale28 | MATa/MATα | This study |
| IMH007 | *S. eubayanus* × *S. cerevisiae* | AS2.4940 × Ale28 | MATa/MATα | This study |

TABLE 2

Hybridization rates and enrichment factors of interspecies (rare) mating between different ploidies of S. eubayanus strain CBS12357 and S. cerevisiae strains IMK439 (1n) and IMX1471 (2n).

| Hybridization time | CBS12357 (spores) × IMK439 (1n × 1n) | | CBS12357 (spores) × IMX1471 (1n × 2n) | | CBS12357 × IMK439 (2n × 1n) | | CBS12357 × IMX1471 (2n × 2n) | |
|---|---|---|---|---|---|---|---|---|
| | Plating[A] | Sorting[B] | Plating | Sorting | Plating | Sorting | Plating | Sorting |
| 24 h | $4.4 \times 10^{-5}$ | $3.1 \times 10^{-2}$ | —[C] | — | — | $4.3 \times 10^{-4}$ | — | — |
| 48 h | $3.2 \times 10^{-5}$ | $6.2 \times 10^{-2}$ | $8 \times 10^{-7}$ | — | $4.6 \times 10^{-6}$ | $2.9 \times 10^{-3}$ | — | — |
| 72 h | $2.5 \times 10^{-5}$ | $3.9 \times 10^{-2}$ | — | — | — | $4.1 \times 10^{-3}$ | — | — |
| 96 h | $6.9 \times 10^{-5}$ | $3.3 \times 10^{-2}$ | $8 \times 10^{-7}$ | $4.3 \times 10^{-4}$ | $7.2 \times 10^{-6}$ | $4.3 \times 10^{-3}$ | $1 \times 10^{-7}$ | — |
| 120 h | $3.4 \times 10^{-4}$ | $2.5 \times 10^{-2}$ | $9 \times 10^{-7}$ | — | $1.9 \times 10^{-6}$ | $1.3 \times 10^{-3}$ | — | — |
| 144 h | $3.2 \times 10^{-4}$ | $3.6 \times 10^{-2}$ | $3 \times 10^{-7}$ | — | $1.6 \times 10^{-6}$ | $4.3 \times 10^{-4}$ | — | — |
| 168 h | $3.0 \times 10^{-4}$ | $2.9 \times 10^{-2}$ | $1.5 \times 10^{-6}$ | — | $4.7 \times 10^{-6}$ | $3.6 \times 10^{-3}$ | — | — |

[A]Determined by plating mating culture on SM + G418
[B]Determined by sorting mating culture on YPD and replica-plating to SM + G418
[C]A hyphen means that no viable hybrids were obtained

TABLE 3

Primers used

| Primer # | Name | Sequence 5' to 3' | Product size (bp) | Description | Origin |
|---|---|---|---|---|---|
| 8570 | Scer F2 | GCGCTTTACATTCAGATCCCGAG (SEQ ID NO: 1) | 150 | S. cerevisiae specific primers | Muir et al., 2011. FEMS Yeast Res 11: 552-563. |
| 8571 | Scer R2 | TAAGTTGGTTGTCAGCAAGATTG (SEQ ID NO: 2) | | | |
| 8572 | Seub F3 | GTCCCTGTACCAATTTAATATTGCGC (SEQ ID NO: 3) | 228 | S. eubayanus specific primers | Pengelly and Wheals, 2013. FEMS Yeast Res 13: 156-161. |
| 8573 | Seub R2 | TTTCACATCTCTTAGTCTTTTCCAGACG (SEQ ID NO: 4) | | | |
| 11 | Matuniv | AGTCACACATCAAGATCGTTTATGG (SEQ ID NO: 5) | MATα: 404 MATa: 504 | S. cerevisiae MAT cassette (α and a) | Huxley, et al., 1990. Trends Gen 6: 236. |
| 12 | Mat-alpha | GCACGGAATATGGGACTACTTCG (SEQ ID NO: 6) | | | |
| 13 | MATa | ACTCCACTTCAAGTAAGAGTTTG (SEQ ID NO: 7) | | | |

The invention claimed is:

1. A method for identifying a hybrid yeast organism, comprising
   (a) providing cells from a first and second yeast parent organism,
       whereby the first and second yeast parent organisms are mating-compatible,
       whereby the first yeast parent organism differs from the second yeast parent organism,
       whereby said first yeast parent organism, but not said second yeast parent organism, carries an auxotrophic marker,
   (b) labelling cells from the second yeast parent organism with a fluorescent dye;
   (c) hybridizing cells from the first yeast parent organism with labelled cells from the second yeast parent organism at a temperature between 5° C. and 15° C.; and
   (d) identifying a hybrid yeast organism as an auxotrophic, labelled cell.

2. The method of claim 1, wherein the cells from the first yeast parent organism and/or the second yeast parent organism are gametes or spores that are labelled after germination.

3. The method of claim 1, wherein the cells from the first yeast parent organism or from the second yeast parent organism are diploid.

4. The method of claim 1, wherein the first and second yeast parent organisms are microorganisms.

5. The method of claim 1, wherein the first and second yeast parent organisms are *Saccharomyces sensu stricto* yeasts.

6. The method of claim 1, wherein the first and second yeast parent organisms are different yeast species and the resulting hybrid is an interspecies hybrid.

7. The method of claim 1, wherein identification of the yeast hybrid organism is performed by fluorescence activated cell sorting (FACS).

8. The method of claim 1, further comprising determining a ploidy of an auxotrophic, labelled cell and identifying a hybrid yeast organism as an auxotrophic, labelled cell having the summed ploidy of the first and second yeast parent organisms.

9. A method for identifying a hybrid yeast organism, comprising
- (a) providing cells from a first and second yeast parent organism,
  - whereby the first and second yeast parent organisms are mating-compatible,
  - whereby the first yeast parent organism differs from the second yeast parent organism,
  - whereby said first yeast parent organism, but not said second yeast parent organism, carries an auxotrophic marker,
- (b) labelling cells from the second yeast parent organism with a fluorescent dye;
- (c) hybridizing cells from the first yeast parent organism with labelled cells from the second yeast parent organism at a temperature that is at least 5° C. below an optimal growth temperature of the first yeast parent organism and/or the second yeast parent organism; and
- (d) identifying a hybrid yeast organism as an auxotrophic, labelled cell.

10. The method of claim 9, wherein the first and second yeast parent organisms are different yeast species and the resulting hybrid is an interspecies hybrid.

* * * * *

SEQUENCE LISTING

<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
gcgctttaca ttcagatccc gag        23

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
taagttggtt gtcagcaaga ttg        23

```
<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
gtccctgtac caatttaata ttgcgc                                              26

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
tttcacatct cttagtcttt tccagacg                                            28

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
agtcacatca agatcgttta tgg                                                 23

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gcacggaata tgggactact tcg                                                 23

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
actccacttc aagtaagagt ttg                                                 23
```